United States Patent
Stayshich et al.

(10) Patent No.: US 12,247,035 B2
(45) Date of Patent: *Mar. 11, 2025

(54) ARTICLES COMPRISING INDOLENAPHTHOPYRANS

(71) Applicant: Transitions Optical, Ltd., Tuam (IE)

(72) Inventors: Ryan Stayshich, Pittsburgh, PA (US); Zachary Smith, Pittsburgh, PA (US); Robert W. Walters, Murrysville, PA (US)

(73) Assignee: Transitions Optical, Ltd., Tuam (IE)

( * ) Notice: Subject to any disclaimer, the term of this patent is extended or adjusted under 35 U.S.C. 154(b) by 929 days.

This patent is subject to a terminal disclaimer.

(21) Appl. No.: 17/416,034

(22) PCT Filed: Dec. 21, 2018

(86) PCT No.: PCT/EP2018/086563
§ 371 (c)(1),
(2) Date: Jun. 18, 2021

(87) PCT Pub. No.: WO2020/126029
PCT Pub. Date: Jun. 25, 2020

(65) Prior Publication Data
US 2022/0064175 A1   Mar. 3, 2022

(51) Int. Cl.
*C09K 9/02* (2006.01)
*C07D 491/052* (2006.01)

(52) U.S. Cl.
CPC ........... *C07D 491/052* (2013.01); *C09K 9/02* (2013.01); *C09K 2211/1018* (2013.01)

(58) Field of Classification Search
None
See application file for complete search history.

(56) References Cited

U.S. PATENT DOCUMENTS

| | | | |
|---|---|---|---|
| 1,189,789 A * | 7/1916 | Stayshich et al. | B60B 9/12 152/48 |
| 6,113,814 A | 9/2000 | Gemert et al. | |
| 6,296,785 B1 | 10/2001 | Nelson et al. | |
| 6,392,043 B1 | 5/2002 | Bourchteine et al. | |
| 6,555,028 B2 | 4/2003 | Walters et al. | |
| 7,262,295 B2 | 8/2007 | Walters et al. | |
| 8,608,988 B2 | 12/2013 | Bowles et al. | |
| 9,028,728 B2 | 5/2015 | Bancroft et al. | |
| 2011/0216273 A1 | 9/2011 | He et al. | |
| 2012/0145973 A1* | 6/2012 | Bancroft | C09K 9/02 544/150 |

FOREIGN PATENT DOCUMENTS

| | | |
|---|---|---|
| EP | 2463280 B1 | 9/2013 |
| JP | 2000229974 A | 8/2000 |
| JP | 2003277381 A | 10/2003 |
| WO | 9923071 A1 | 5/1999 |

OTHER PUBLICATIONS

Hansch et al., "A Survey of Hammett Substituent Constants and Resonance and Field Parameters", Chem. Rev., 1991, pp. 165-195, vol. 91.

* cited by examiner

*Primary Examiner* — Sheeba Ahmed
(74) *Attorney, Agent, or Firm* — The Webb Law Firm

(57) ABSTRACT

Provided is an article which transitions from a first state to a second state in response to actinic radiation. The article includes an indolenaphthopyran, wherein in the first state the article exhibits a percent transmission of greater than 80 percent, and in the second state the article exhibits a percent transmission of between 35 and 75 percent, and a $\tau_{SB}$ value of less than 20 percent. The article can be a photochromic article selected from ophthalmic articles, display articles, windows, mirrors, active liquid crystal cell articles, and passive liquid crystal cell articles.

15 Claims, 1 Drawing Sheet

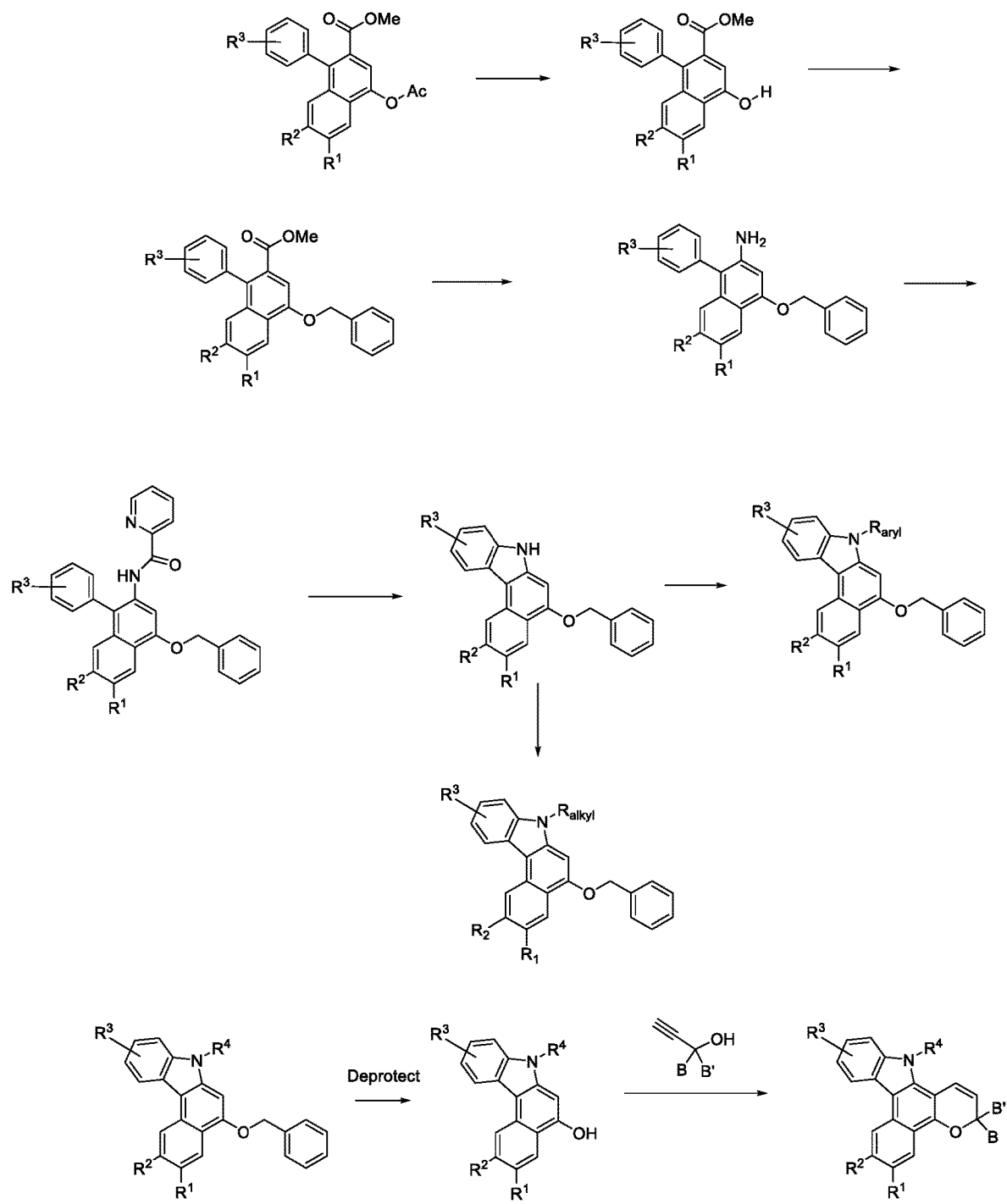

ARTICLES COMPRISING INDOLENAPHTHOPYRANS

CROSS-REFERENCE TO RELATED APPLICATION

This application is the United States national phase of International Application No. PCT/EP2018/086563 filed Dec. 21, 2018, the disclosure of which is hereby incorporated by reference in its entirety.

FIELD

The present invention is directed to articles, such as optical articles, comprising certain indolenaphthopyran compounds, in particular photochromic indolenaphthopyrans.

BACKGROUND

Photochromic compounds undergo a transformation from one state (or form) to another state in response to certain wavelengths of electromagnetic radiation (e.g., "actinic radiation"). Each state has a characteristic absorption spectrum. For example, many photochromic compounds transform from an unactivated (e.g., bleached or substantially colorless) first state to an activated (e.g., tinted or darkened) second state upon exposure to actinic radiation. When the actinic radiation is removed, the photochromic compounds reversibly transform from the second, activated state back to the first, unactivated state.

Photochromic compounds can be characterized with regard to various properties, such as but not limited to: fade rate; change in optical density ($\Delta OD$); the change in optical density ($\Delta OD$) at saturation; sensitivity ($\Delta OD/Min$); the efficiency at which the photochromic compound absorbs radiation required to activate the photochromic compound (chromaticity); and dichroic properties such as in the case of photochromic-dichroic compounds, which can be quantified with regard to absorption ratio (AR) values. The change in optical density measures the change from the unactivated state to the activated state.

Some photochromic compounds have a bimodal absorption profile, having an absorption band "A" (hereinafter referred to as "A band") which is of greater intensity than the absorption band "B" (hereinafter referred to as "B band"). The absorption of the A band generally occurs in the 420-500 nanometer wavelength region while the absorption of B band occurs in the 500-650 nanometer wavelength region of the activated visible spectrum.

The yellow colored naphthopyrans have a high b* value in the activated (i.e., colored) state, but these compounds have inherent weakness in durability and often degrade at rates much faster than purple or blue photochromic compounds of the indeno-fused naphthopyran families. Broad band absorbing indeno-fused compounds have been used to overcome the limitations of yellow naphthopyrans, but indeno-fused naphthopyrans that are yellow (high b*) in the activated (i.e., colored) state are still difficult to obtain.

The deleterious health effects of blue light such as cataracts, macular degeneration, and disruption of circadian rhythm are well documented. Many fixed tint optical products have been produced to help block harmful blue light both from indoor sources (such as from fluorescent lighting) and outdoor exposure to sunlight which has a high level of blue light present. Such conventional optical products generally employ static yellow dyes or tints to serve as blue light blockers. However, the static yellow color of such optical products comprising these static yellow dyes is not aesthetically desirable, particularly when worn indoors. Moreover, such optical products do not provide an increase in protection from blue light present in sunlight when worn outdoors. That is, the conventional optical articles that rely on static yellow dyes or tints for blue light blocking have a yellow color both indoors and outdoors, and provide the same level of blue light blocking both indoors and outdoors.

Thus, it would be desirable to provide an article, such as an optical article, which is substantially clear and somewhat blue light blocking in an indoor environment, but colors and becomes more blue light blocking upon exposure to sunlight in an outdoor environment.

SUMMARY

The present invention is directed to an article which transitions from a first state to a second state in response to actinic radiation. The article comprises an indolenaphthopyran, wherein in the first state the article exhibits a percent transmission of greater than 80 percent, and in the second state the article exhibits a percent transmission of between 35 and 75 percent, and a $\tau_{SB}$ value of less than 20.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWING

FIG. 1 illustrates a general scheme, Scheme 1, of an exemplary method for preparing photochromic indolenaphthopyran compounds useful in the preparation of the articles of the invention.

DETAILED DESCRIPTION

As used herein, the articles "a", "an", and "the" include plural referents unless otherwise expressly and unequivocally limited to one referent.

As used herein, the term "includes" is synonymous with "comprises."

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as divalent linking groups, are inclusive of other appropriate orientations, such as, but not limited to, right-to-left orientations. For purposes of non-limiting illustration, the left-to-right representation of the divalent linking group

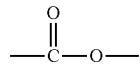

or equivalently —C(O)O—, is inclusive of the right-to-left representation thereof,

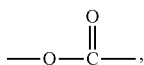

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about." By "about" is meant plus or minus twenty-five percent of the stated value, such as plus or minus ten percent of the stated value. However, this should not be considered as limiting to any analysis of the values under the doctrine of equivalents.

As used herein, molecular weight values of polymers, such as weight average molecular weights (Mw) and number average molecular weights (Mn), are determined by gel permeation chromatography using appropriate standards, such as polystyrene standards.

As used herein, the term "polymer" means homopolymers (e.g., prepared from a single monomer species), copolymers (e.g., prepared from at least two monomer species), and graft polymers.

As used herein, the term "(meth)acrylate" and similar terms, such as "(meth)acrylic acid ester" means derivatives of acrylic acid and methacrylic acid, inclusive of acrylate esters, methacrylate esters, acrylamides, methacrylamides, acrylic acid and methacrylic acid. As used herein, the term "(meth)acrylic acid" means methacrylic acid and/or acrylic acid.

The photochromic compounds of the present invention are, with some embodiments, also referred to herein as photochromic-dichroic compounds (such as, when they include one or more mesogen-containing groups, such as L).

The photochromic compounds of the present invention, as described herein, including, but not limited to, photochromic compounds represented by Formula (I) and Formula (Ta), in each case can optionally further include one or more coproducts, resulting from the synthesis of such compounds.

As used herein, the term "photochromic" and similar terms, such as "photochromic compound" means having an absorption spectrum for at least visible radiation that varies in response to absorption of at least actinic radiation. Further, as used herein the term "photochromic material" means any substance that is adapted to display photochromic properties (such as, adapted to have an absorption spectrum for at least visible radiation that varies in response to absorption of at least actinic radiation) and which includes at least one photochromic compound.

As used herein, the term "actinic radiation" means electromagnetic radiation that is capable of causing a response in a material, such as, but not limited to, transforming a photochromic material from one form or state to another as will be discussed in further detail herein.

As used herein, the term "dichroic" means capable of absorbing one of two orthogonal plane polarized components of at least transmitted radiation more strongly than the other.

As used herein, the term "photochromic-dichroic" and similar terms, such as "photochromic-dichroic compound", means possessing and/or providing both photochromic properties (i.e., having an absorption spectrum for at least visible radiation that varies in response to at least actinic radiation), and dichroic properties (i.e., capable of absorbing one of two orthogonal plane polarized components of at least transmitted radiation more strongly than the other).

As used herein, and unless stated otherwise or otherwise limited, the term "photochromic material" includes thermally reversible photochromic materials and compounds and non-thermally reversible photochromic materials and compounds. The term "thermally reversible photochromic compounds/materials" as used herein means compounds/materials capable of converting from a first state, for example a "clear state," to a second state, for example a "colored state," in response to actinic radiation, and reverting back to the first state in response to thermal energy. The term "non-thermally reversible photochromic compounds/materials" as used herein means compounds/materials capable of converting from a first state, for example a "clear state," to a second state, for example a "colored state," in response to actinic radiation, and reverting back to the first state in response to actinic radiation of substantially the same wavelength(s) as the absorption(s) of the colored state (e.g., discontinuing exposure to such actinic radiation).

As used herein, to modify the term "state," the terms "first" and "second" are not intended to refer to any particular order or chronology, but instead refer to two different conditions or properties. For purposes of non-limiting illustration, the first state and the second state of a photochromic compound can differ with respect to at least one optical property, such as but not limited to the absorption of visible and/or UV radiation. Thus, according to various non-limiting embodiments disclosed herein, the photochromic compounds of the present invention can have a different absorption spectrum in each of the first and second state. For example, while not limiting herein, a photochromic compound of the present invention can be clear in the first state and colored in the second state. Alternatively, a photochromic compound of the present invention can have a first color in the first state and a second color in the second state.

As used herein, the term "optical" means pertaining to or associated with light and/or vision. For example, according to various non-limiting embodiments disclosed herein, the optical article or element or device can be chosen from ophthalmic articles, elements and devices; display articles, elements and devices; windows; mirrors; or active and passive liquid crystal cell articles, elements and devices.

As used herein, the term "ophthalmic" means pertaining to or associated with the eye and vision. Non-limiting examples of ophthalmic articles or elements include corrective and non-corrective lenses, including single vision or multi-vision lenses, which can be either segmented or non-segmented multi-vision lenses (such as, but not limited to, bifocal lenses, trifocal lenses and progressive lenses), as well as other elements used to correct, protect, or enhance (cosmetically or otherwise) vision, including without limitation, contact lenses, intra-ocular lenses, magnifying lenses, and protective lenses or visors.

As used herein, the term "display" means the visible or machine-readable representation of information in words, numbers, symbols, designs or drawings. Non-limiting examples of display elements include screens, monitors, and security elements, such as security marks.

As used herein, the term "window" means an aperture adapted to permit the transmission of radiation therethrough. Non-limiting examples of windows include automotive and aircraft transparencies, windshields, filters, shutters, and optical switches.

As used herein, the term "mirror" means a surface that specularly reflects a large fraction of incident light.

As used herein, the term "liquid crystal cell" refers to a structure containing a liquid crystal material that is capable of being ordered. A non-limiting example of a liquid crystal cell element is a liquid crystal display.

As used herein, the terms "formed over", "deposited over", "provided over", "applied over", "residing over", or "positioned over" mean formed, deposited, provided, applied, residing, or positioned on but not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, recitations relating to ring positions such as, but not limited to, position-x (e.g., position-3 or position-13) means a particular position in the ring structure, such as the core skeletal structure, of a chemical compound, such as the indolenaphthopyran photochromic compounds of the present invention, and which are depicted herein in accordance with some embodiments by numbers within the ring structures of representative chemical formulas such as, but not limited to Formulas (I) and/or (Ta).

By "core skeletal structure" is meant a compound comprising at least the skeletal structure depicted in the associated Formula. The core skeletal structure is provided for purposes of identifying numbered ring positions. However, it is to be understood that, unless specifically shown to the contrary, the core skeletal structure(s) can have one or more atoms or one or more groups (not specifically illustrated on the corresponding Formula) bonded to one or more of the numbered ring positions on the core skeletal structure, which can be the same or different from one another.

The photochromic compounds of the present invention are referred to herein with reference to the term "core skeletal structure," which can be represented by one or more formulas, such as but not limited to Formulas (I) and/or (Ta).

All documents or portions of documents, such as but not limited to issued patents and patent applications, referred to herein, and unless otherwise indicated, are to be considered to be "incorporated by reference" in their entirety.

As used herein, recitations of "substituted" group, means a group including, but not limited to, alkyl group, heterocycloalkyl group, aryl group, and/or heteroaryl group, in which at least one hydrogen thereof has been replaced or substituted with a group that is other than hydrogen, such as, but not limited to, alkoxy groups; halo groups (e.g., F, Cl, I, and Br); hydroxyl groups; thiol groups; alkylthio groups; ketone groups; aldehyde groups; ester groups; carboxylic acid groups; phosphoric acid groups; phosphoric acid ester groups; sulfonic acid groups; sulfonic acid ester groups; nitro groups; cyano groups; alkyl groups (including aralkyl groups); alkenyl groups; alkynyl groups; haloalkyl groups; perhaloalkyl groups; heterocycloalkyl groups; aryl groups (including alkaryl groups, including hydroxyl substituted aryl, such as phenol, and including poly-fused-ring aryl); heteroaryl groups (including poly-fused-ring heteroaryl groups); amino groups, such as —N($R^{11'}$)($R^{12'}$) where $R^{11'}$ and $R^{12'}$ are each independently selected, for example, from hydrogen, alkyl, heterocycloalkyl, aryl, or heteroaryl; carboxylate groups; siloxane groups; alkoxysilane groups; polysiloxane groups; amide groups; carbamate groups; carbonate groups; urea groups; polyester groups; polyether groups; polycarbonate groups; polyurethane groups; acrylate groups; methacrylate groups; nitrogen-containing heterocycles; or combinations thereof, including those classes and examples as described further herein.

"Aryl group" refers to an aromatic cyclic monovalent hydrocarbon radical, and the term "aromatic" refers to a cyclically conjugated hydrocarbon with a stability (due to delocalization) that is significantly greater than that of a hypothetical localized structure. Examples of aryl groups include $C_6$-$C_{14}$ aryl groups, such as, but not limited to, phenyl, naphthyl, phenanthryl, and anthracenyl.

As used herein, recitations of "halo substituted" and related terms (such as, but not limited to, haloalkyl groups, haloalkenyl groups, haloalkynyl groups, haloaryl groups and halo-heteroaryl groups) means a group in which at least one, and up to and including all of the available hydrogen groups thereof is substituted with a halo group. The term "halo-substituted" is inclusive of "perhalo-substituted." As used herein, the term perhalo-substituted group and related terms (such as, but not limited to, perhaloalkyl groups, perhaloalkenyl groups, perhaloalkynyl groups, perhaloaryl groups or perhalo-heteroaryl groups) means a group in which all of the available hydrogen groups thereof are substituted with a halo group. For example, perhalomethyl is —$CX_3$; perhalophenyl is —$C_6X_5$, where X represents one or more halo groups, such as, but not limited to F, Cl or Br.

As used herein, recitations of "linear or branched" groups, such as linear or branched alkyl, are herein understood to include: groups that are linear (or "straight chain"), such as linear $C_1$-$C_{25}$ alkyl groups; and groups that are appropriately branched, such as branched $C_3$-$C_{25}$ alkyl groups.

The term "alkyl" as used herein means linear or branched, cyclic or acyclic $C_1$-$C_{25}$ alkyl. Linear or branched alkyl can include $C_1$-$C_{25}$ alkyl, such as $C_1$-$C_{20}$ alkyl, such as $C_2$-$C_{10}$ alkyl, such as $C_1$-$C_{12}$ alkyl, such as $C_1$-$C_6$ alkyl. Examples of alkyl groups from which the various alkyl groups of the present invention can be selected from, include, but are not limited to, those recited further herein. Alkyl groups can include "cycloalkyl" groups. The term "cycloalkyl" as used herein means groups that are appropriately cyclic, such as, but not limited to, $C_3$-$C_{12}$ cycloalkyl (including, but not limited to, cyclic $C_5$-$C_7$ alkyl, or cyclic $C_3$-$C_{10}$ alkyl) groups. Examples of cycloalkyl groups include, but are not limited to, those recited further herein. The term "cycloalkyl" as used herein also includes: bridged ring polycycloalkyl groups (or bridged ring polycyclic alkyl groups), such as, but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein means groups that are appropriately cyclic, such as, but not limited to, $C_2$-$C_{12}$ heterocycloalkyl groups, such as $C_5$-$C_7$ heterocycloalkyl groups, such as $C_2$-$C_{10}$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein also includes: bridged ring polycyclic heterocycloalkyl groups, such as, but not limited to, 7-oxabicyclo[2.2.1]heptanyl; and fused ring polycyclic heterocycloalkyl groups, such as, but not limited to, octahydrocyclopenta[b]pyranyl, and octahydro-1H-isochromenyl.

The term "heteroaryl" as used herein includes, but is not limited to, $C_3$-$C_{18}$ heteroaryl, such as, but not limited to, $C_3$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group.

Examples of heteroaryl groups include, but are not limited to, furanyl, pyranyl, pyridinyl, isoquinoline, and pyrimidinyl.

As used herein, the term "fused ring polycyclic-aryl-alkyl group" and similar terms, such as fused ring polycyclic-alkyl-aryl group, fused ring polycyclo-aryl-alkyl group, and fused ring polycyclo-alkyl-aryl group means a fused ring polycyclic group that includes at least one aryl ring and at least one cycloalkyl ring that are fused together to form a fused ring structure. For purposes of non-limiting illustration, examples of fused ring polycyclic-aryl-alkyl groups include, but are not limited to, indenyl, 9H-fluorenyl, cyclopentanaphthenyl, and indacenyl.

The term "aralkyl" as used herein includes, but is not limited to, $C_6$-$C_{24}$ aralkyl, such as, but not limited to, $C_6$-$C_{10}$ aralkyl, and means an alkyl group substituted with an aryl group. Examples of aralkyl groups include, but are not limited to, benzyl and phenethyl.

Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are not limited to, vinyl, allyl and propenyl. Representative alkynyl groups include, but are not limited to, ethynyl, 1-propynyl, 2-propynyl, 1-butynyl, and 2-butynyl. Representative cycloalkyl groups include, but are not limited to, cyclopropyl, cyclobutyl, cyclopentyl, cyclohexyl, and cyclooctyl substituents. Representative heterocycloalkyl groups include, but are not limited to, imidazolyl, tetrahydrofuranyl, tetrahydropyranyl and piperidinyl. Representative aryl groups include, but are not limited to, phenyl, naphthyl, anthracynyl, phenanthrenyl, and tetracenyl (including structural isomers thereof). Representative heteroaryl groups include, but are not limited to, furanyl, pyranyl, pyridinyl, isoquinolinyl, and pyrimidinyl. Representative aralkyl groups include, but are not limited to, benzyl and phenethyl.

The term "nitrogen-containing heterocycle" as used herein includes, but is not limited to, a nitrogen-containing ring wherein the nitrogen-containing ring is bonded through a ring nitrogen. Examples of nitrogen-containing heterocycles include, but are not limited to, cyclic aminos, such as morpholino, piperidino, and pyrrolidino; and heteroaromatics, such as imidazole, pyrrole, indole, and carbazole.

As used herein, "at least one of" is synonymous with "one or more of", whether the elements are listed conjunctively or disjunctively. For example, the phrases "at least one of A, B, and C" and "at least one of A, B, or C" each mean any one of A, B, or C, or any combination of any two or more of A, B, or C. For example, A alone; or B alone; or C alone; or A and B; or A and C; or B and C; or all of A, B, and C.

As used herein, "selected from" is synonymous with "chosen from", whether the elements are listed conjunctively or disjunctively. Further, the phrases "selected from A, B, and C" and "selected from A, B, or C" each mean any one of A, B, or C, or any combination of any two or more of A, B, or C. For example, A alone; or B alone; or C alone; or A and B; or A and C; or B and C; or all of A, B, and C.

The discussion of the invention may describe certain features as being "particularly" or "preferably" within certain limitations (e.g., "preferably", "more preferably", or "even more preferably", within certain limitations). It is to be understood that the invention is not limited to these particular or preferred limitations but encompasses the entire scope of the disclosure.

The invention comprises, consists of, or consists essentially of, the following aspects of the invention, in any combination. As previously mentioned, the present invention is directed to an article which transitions from a first state to a second state in response to exposure to electromagnetic radiation, for example, actinic radiation. In the first state the article exhibits a percent transmission of greater than 80 percent, such as greater than 85 percent, such as greater than 88 percent. In the second state the article exhibits a percent transmission of between 35 and 75 percent, such as between 40 and 70 percent, such as between 45 and 65 percent, and a $\tau_{SB}$ value of less than 20 percent, such as less than 15 percent, such as less than 10 percent. For example, in the second state the article can exhibit a $\tau_{SB}$ value of 3.0 percent to less than 20 percent, such as 4.0 percent to less than 20 percent, such as 5.0 percent to less than 20 percent. By the term "percent transmission" is meant the percent of spectral light transmitted through a transparent article as perceived by the human eye as determined using the CIE Y value in accordance with CIE 15: 2004 colorimetry using a D65 illuminant and 10° observer. Percent transmission also may be referred to herein in the specification and examples as "% T". The $\tau_{SB}$ value is the solar blue light transmission which is the result of the mean of the spectral transmission between 380 and 500 nanometers and appropriate weighting functions. See ISO 12311: 2013(E), Subsection 7.4.

For example, the article of the present invention can be a photochromic article where the first state is the unactivated, generally colorless state such as when the article is not exposed to actinic radiation. The percent transmission value in this first state is greater than 80 percent. Upon exposure to actinic radiation, the photochromic article transitions to a second, activated or colored state where the percent transmission decreases in response to the actinic radiation. The percent transmission in this second state is decreased to a value ranging from 35 to 75 percent. As the percent transmission decreases in response to actinic radiation in the second state, the $\tau_{SB}$ value (i.e., the solar blue light transmission) also decreases to less than 20 percent. Thus, the article of the present invention transitions in response to actinic radiation from a generally clear first state to a colored second state with enhanced blue light blocking. Upon removal of the actinic radiation source, the article can revert back to the first unactivated and clear or colorless state.

Further, the article of the present invention can have a b* value in the first state of ranging from −5 to 15, such as from −5 to 10, such as from −5 to 5. Also, the article of the present invention can have a b* value in the first state of ranging from 0 to 15, such as from 0 to 10, such as from 0 to 5. The b* value as used herein in the specification and the claims refers to the b* value measured in accordance with in accordance with CIE 15: 2004 space colorimetry, employing a D 65 illuminant and 10° observer, using the Hunter UltraScan Pro unit. The b* axis represents the blue-yellow component, with blue in the negative direction and yellow in the positive direction. The b* values as stated immediately above indicate that the article of the present invention generally has no or very little yellow color in the first state.

As previously mentioned, the article of the present invention comprises an indolenaphthopyran, such as a photochromic indolenaphthopyran comprising the core skeletal structure represented by the following Formula (I). The indolenaphthopyran employed in the article of the present invention can be represented by one or more of the core skeletal structures described below.

Each available numbered ring position (e.g., 1, 2, 5, 8, 9, 10, 11, and/or 12) of the core skeletal structure of Formula (I) can have covalently bonded thereto hydrogen or a group other than hydrogen, for example, such as a group described herein. Examples of such groups are described below.

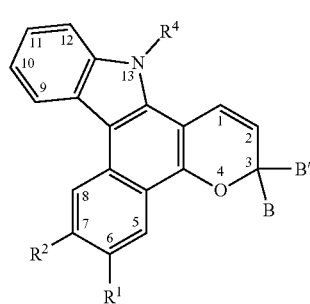

(I)

With reference to Formula (I), $R^1$ and $R^2$ are each independently hydrogen, substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, a nitrogen containing heterocycle, substituted or unsubstituted alkyl, substituted or unsubstituted aryl, —NHC(O)$R^a$, or —OC(O)$R^a$. Examples of groups from which $R^a$ can be selected include substituted or unsubstituted alkyl, substituted or unsubstituted aryl, substituted or unsubstituted heteroaryl, substituted or unsubstituted alkoxy, substituted or unsubstituted aryloxy, substituted or unsubstituted alkylthio, or substituted or unsubstituted arylthio. $R^4$ is selected from hydrogen, substituted or unsubstituted alkyl, substituted or unsubstituted heterocycloalkyl, allyl, substituted or unsubstituted aryl, or substituted or unsubstituted heteroaryl. For example, $R^4$ can be substituted or unsubstituted phenyl or substituted or unsubstituted alkyl. B and B' are each independently substituted or unsubstituted aryl, or substituted or unsubstituted heteroaryl. Each substituted aryl or substituted heteroaryl can be substituted with a group having a Hammett $\sigma_p$ value of greater than −0.50. The relative strength of electron donor groups is frequently described by Hammett Sigma values, or $\sigma_p$ values. A list of Hammett $\sigma_p$ values for various substituents can be found in "A Survey of Hammett Substituent Constants and Resonance and Field Parameters", C. Hansch, A. Leo, and R. W. Taft, *Chem. Rev.*, 1991, 91, 165-195, which disclosure is incorporated herein by reference. Non-limiting examples of suitable substituents having a Hammett $\sigma_p$ value of greater than −0.50 include halo groups (i.e., fluoro or bromo), alkyl, perhaloalkyl, phenyl, methyl, phenyl ether, aralkyl, ethoxy, methoxy, p-aminophenyl, arylthio, alkylthio, amide, carboxylate, aryl, heteroaryl, hydroxyl, cyano, or ester.

Examples of groups from which $R^1$ can be selected include, but are not limited to, substituted or unsubstituted alkoxy. Examples of groups from which $R^2$ can be selected include, but are not limited to, substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, or a nitrogen-containing heterocycle. B and B' can each independently be substituted aryl or substituted heteroaryl. Each substituted aryl or substituted heteroaryl can be substituted with a group having a Hammett $\sigma_p$ value of −0.5 to 0.8. B and B' can each independently be substituted or unsubstituted phenyl. Each phenyl substituent can be selected from alkoxy, halo, alkyl, or aryloxy. $R^1$ and $R^2$ taken together can form a cyclic structure, such as a ring structure.

Additionally or alternatively, the article of the present invention can comprise indolenaphthopyran compounds represented by the core skeletal structure of Formula (Ta):

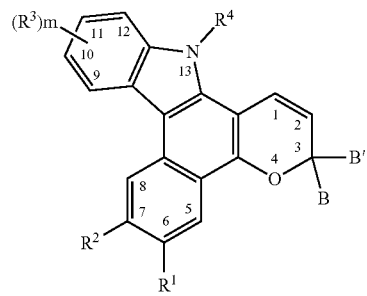

(Ia)

With reference to Formula (Ta), $R^1$, $R^2$, $R^4$, B and B' are as previously described with respect to Formula (I).

As described above, the remaining numbered ring positions (e.g., 1, 2, 5, and/or 8) of the core skeletal structure of Formula (Ta) without a specifically shown substituent can have covalently bonded thereto hydrogen or a group other than hydrogen, for example, such as a group described herein.

With further reference to Formula (Ta), m is 0 to 4, and $R^3$ independently for each m, is hydroxyl; cyano; (meth) acrylate; amino or nitrogen-containing heterocycle; a mesogen-containing group $L^1$; substituted or unsubstituted alkyl; substituted or unsubstituted alkenyl; substituted or unsubstituted alkynyl; a halo group; a perhalo group; boronic ester or boronic acid; polyether, polyester, polycarbonate, or polyurethane; substituted or unsubstituted aryl; substituted or unsubstituted heterocycloalkyl; substituted or unsubstituted heteroaryl; substituted or unsubstituted alkoxy or substituted or unsubstituted aryloxy; substituted or unsubstituted alkylthio or substituted or unsubstituted arylthio; ketone, aldehyde, ester, carboxylic acid, carboxylate, or amide; carbonate, carbamate, or urea; or siloxane, alkoxysilane, or polysiloxane. For example, $R^3$ can be cyano; a halo group; haloalkyl; perhaloalkyl; substituted or unsubstituted aryl; or substituted or unsubstituted heteroaryl. For example, $R^3$ can be at the 11-position. For example, $R^3$ can be at the 10-position and be a mesogen-containing group $L^1$.

With further reference to Formula (Ta), each mesogen-containing group $L^1$ can independently be represented by the following Formula (II), —[S$^1$]$_c$-[Q$^1$-[S$^2$]$_d$]$_{d'}$-[Q$^2$-[S$^3$]$_e$]$_{e'}$-[Q$^3$-[S$^4$]$_f$]$_{f'}$—R    Formula (II)

$Q^1$, $Q^2$, and $Q^3$ for each occurrence, are independently a divalent group selected from the group consisting of unsubstituted aryl, substituted aryl, unsubstituted cycloalkyl, and substituted cycloalkyl. The aryl substituents and cycloalkyl substituents can each independently be selected from the group consisting of liquid crystal mesogens, halogen, alkyl, alkoxy, alkylamino, dialkylamino, alkylthio, alkoxycarbonyl, alkylcarbonyl, alkoxycarbonyloxy, aryloxycarbonyloxy, perfluoroalkyl, and perfluoroalkoxy. With further reference to Formula (II), c, d, e, and f are each independently an integer of 0 to 3; and each $S^1$, $S^2$, $S^3$, and $S^4$ is independently chosen for each occurrence from a spacer unit selected from the group consisting of: (i) —C(Z)$_2$—, —N(Z)—, —C(Z)=C(Z)—, —C(Z)=N—, wherein Z for each occurrence is independently selected from the group consisting of hydrogen, alkyl, or aryl; (ii) —Si(CH$_3$)$_2$—, —Si(CH$_3$)$_2$O—; and (iii) —O—, —C(=O)—, —C≡C—, —N═N—, —S—, —S(═O)—, —(O═)S(═O)—, —(O═)S(═O)O—, —O(O═)S(═O)O—, provided that when two spacer units comprising heteroatoms are linked together the spacer units are linked so that heteroatoms are not directly linked to each other. With further reference to Formula (II), R is alkyl. With further reference to Formula (II), d', e' and f are each independently 0, 1, 2, 3, and 4, provided that the sum of d'+e'+f is at least 1.

As used herein, the term "polysiloxane", such as with regard to substituents of various groups of the photochromic compounds of the present invention, includes a material represented by the following Formula (G):

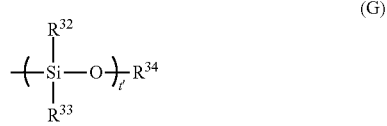

(G)

With reference to Formula (G), subscript t' is from 2 to 200, such as from 2 to 100, or 2 to 50, or from 2 to 25, or from 2 to 15, or from 2 to 10, or from 2 to 5, in each case inclusive of the recited values. With further reference to Formula (G): $R^{32}$ and $R^{33}$, for each t', are each independently selected from alkyl or aryl; and $R^{34}$ is selected from hydrogen, alkyl, or aryl. With some embodiments: $R^{32}$ and $R^{33}$ for each t', are each independently selected from methyl, ethyl, or phenyl; and $R^{34}$ is selected from hydrogen, methyl, ethyl, or phenyl.

As used herein, the term "polysiloxane" such as with regard to substituents of various groups of the photochromic compounds of the present invention, alternatively to or in addition to a material represented by Formula (G), includes a material represented by the following Formula (H):

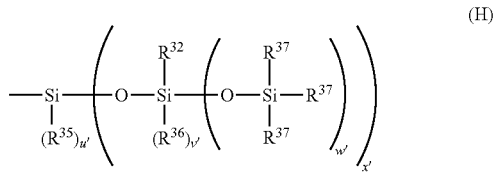

(H)

With reference to Formula (H), subscript u' is 0-2 and subscript x' is 1-3, provided that u'+x' is 3; and subscript v' is 0-2 and subscript w' is 1-3, provided that v'+w' is 3. With further reference to Formula (H), $R^{35}$ independently for each u', $R^{36}$ independently for each v' and each x', and each $R^{37}$ independently for each w' and each x', are in each case independently selected from alkyl (such as, but not limited to, methyl or ethyl) or aryl (such as, but not limited to, phenyl).

With some embodiments, the article of the present invention can comprise the compounds of the aforementioned Formulas (I) and/or (Ta) either alone or in combination with one or more other photochromic compounds. For example, the article of the present invention can comprise the compounds of the aforementioned Formulas (I) and/or (Ta) in conjunction with one or more other photochromic compounds having activated absorption maxima within the range of 300 to 1,000 nanometers. Further, the compounds of the aforementioned Formulas (I) and/or (Ta) can be used in conjunction with one or more complementary conventional polymerizable or compatiblized photochromic compounds, such as for example, those disclosed in U.S. Pat. No. 6,113,814 (at col. 2, line 39 to col. 8, line 41), and U.S. Pat. No. 6,555,028 (at col. 2, line 65 to col. 12, line 56).

Further, the compounds of Formulas (I) and/or (Ta) can be used in combination with a mixture of other photochromic compounds. For example, although not limiting herein, mixtures of photochromic compounds can be used to attain certain activated colors.

Examples of classes of other photochromic compounds that can be used in combination with the compounds of Formulas (I) and/or (Ta) in the preparation of the articles of the present invention, include, but are not limited to, indeno-fused naphthopyrans, naphtho[1,2-b]pyrans, naphtho[2,1-b]pyrans, spirofluoreno[1,2-b]pyrans, phenanthrenopyrans, quinolinopyrans, fluoroanthenopyrans, spiropyrans, benzoxazines, naphthoxazines, spiro(indoline)naphthoxazines, spiro(indoline)pyridobenzoxazines, spiro(indoline)fluoranthenoxazines, spiro(indoline)quinoxazines, fulgides, fulgimides, diarylethenes, diarylalkylethenes, diarylalkenylethenes, thermally reversible photochromic compounds, and non-thermally reversible photochromic compounds, and mixtures thereof. Further examples of other photochromic compounds that can be used in combination with the compounds of Formulas (I) and/or (Ta) can include, but are not limited to, those disclosed at column 34, line 20 through column 35, line 13 of U.S. Pat. No. 9,028,728 B2.

The indolenaphthopyran compounds useful in the articles of the present invention can be prepared in accordance with art-recognized methods as follows. For purposes of non-limiting illustration and with reference to FIG. 1, general synthetic Scheme 1, the preparation of photochromic compounds according to the present invention is described as follows. Further detailed descriptions of the preparation of photochromic compounds of the present invention are provided further herein in the Examples. In FIG. 1, the various groups, such as $R^1$, $R^2$, $R^3$, $R^4$, B, B', $R_{aryl}$, and $R_{alkyl}$ of the various intermediates, reactants, and/or compounds depicted, are each as described herein, and/or represent precursors of such groups.

The synthesis of compounds depicted below as Formula III has been described in numerous references such as U.S. Pat. No. 6,296,785 or 7,262,295, with varying substituents.

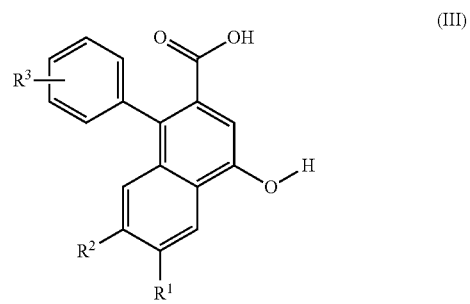

(III)

The hydroxyl group and the carboxylic acid group can be benzylated by reacting with benzyl chloride and a base such as sodium or potassium carbonate. The carboxylic ester that is formed can then be converted to the carboxylic acid by either acid or basic methods for ester hydrolysis. The resulting product is depicted below as Formula IIIa.

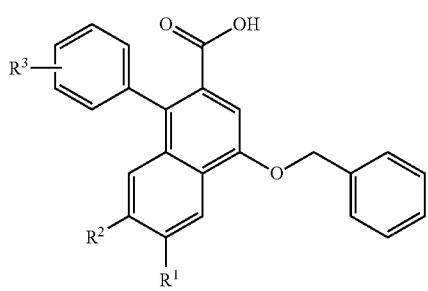

(IIIa)

The carboxylic acid group can then be converted to an NH₂ group via Curtius rearrangement conditions using diphenyl phosphorylazide which generates the isocyanate group followed by hydrolysis to yield the amine group, as depicted below in Formula IIIb.

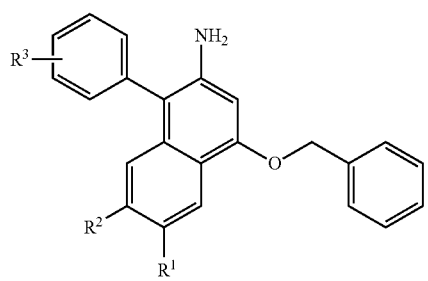

(IIIb)

The amine group is converted to an indole by first forming the picolinamide group by traditional amide forming reactions such as reacting the amine with acid chlorides, esters, or carboxylic acid groups. Reaction of the amine with picolinoyl chloride with a base such as triethylamine gives the picolinamide, as depicted in Formula IIIc, in high yields. The picolinamide can be cyclized to the indole, as depicted in Formula IIId, by use of a copper catalyst as described in Takumatso, K. et al. *Org. Lett.* 2014, 16, 2892. See reaction depicted below.

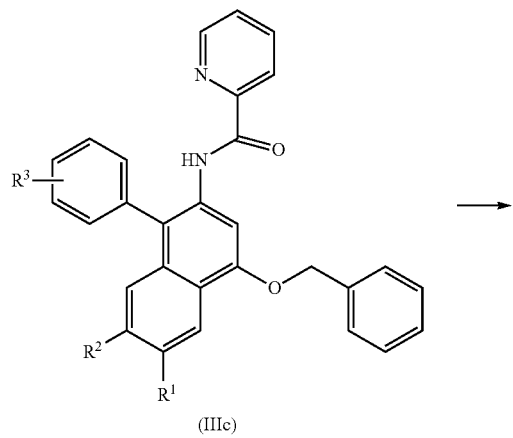

(IIIc)

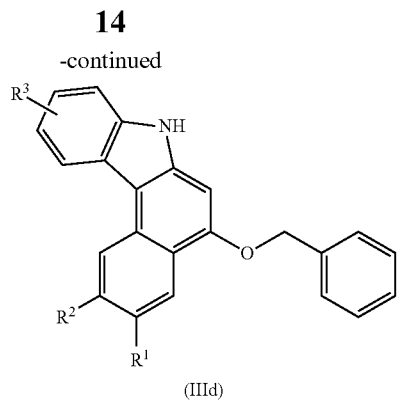

(IIId)

The indole ring as depicted in Formula IIId can also be formed by reacting the amine of Formula IIIb with Tosyl (Ts) chloride or anhydride to form a N-Ts group, as depicted in Formula IIIe. This group can be cyclized with palladium catalyst as described in Youn, S. W. *Org. Lett.* 2011, 13, 3738. See reaction depicted below.

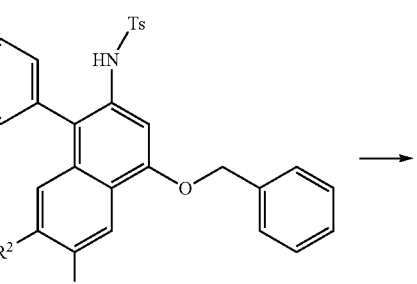

(IIIe)

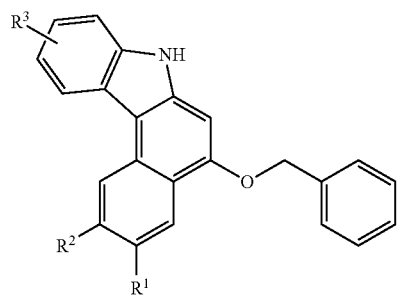

(IIId)

Alternatively, the amino group of Formula IIIb can be converted to an azide group, as depicted in Formula IIIf, by forming the diazonium salt under Sandmeyer conditions followed by displacement with a salt of azide such as sodium azide. The indole group of Formula IIId can then be formed by exposure to UV light in a solvent such as THF. See reaction depicted below.

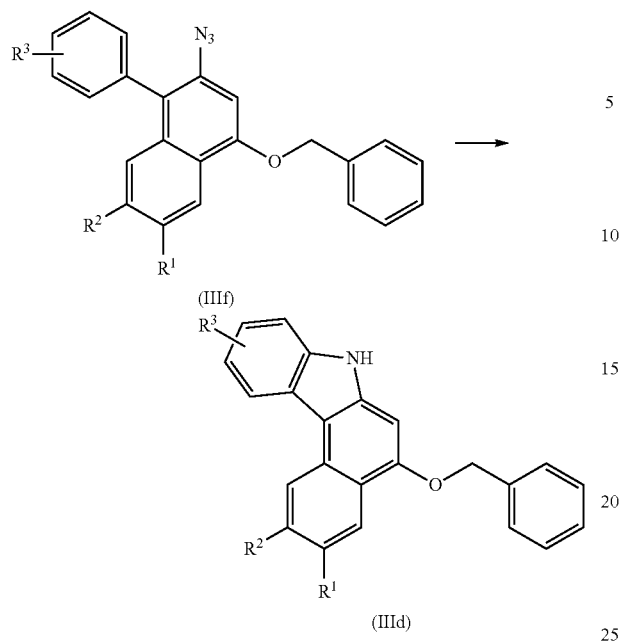

(IIIf)

(IIId)

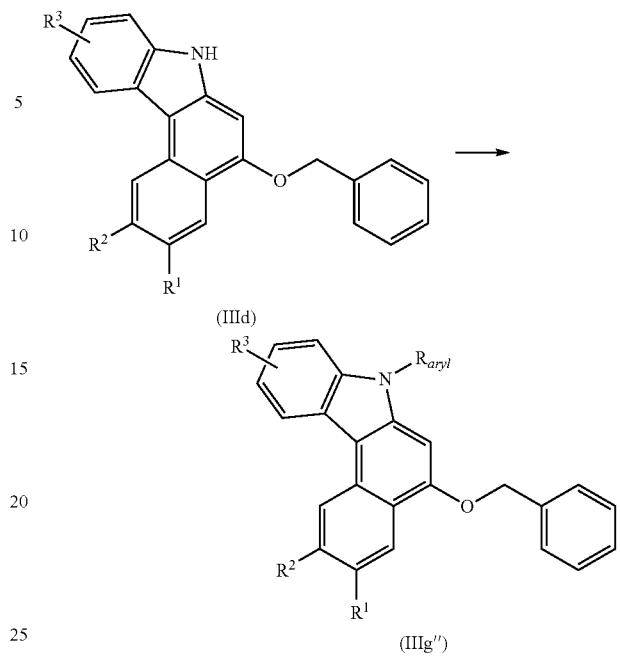

(IIId)

(IIIg″)

The alkylation of the indole group as depicted in Formula IIIg' can be accomplished by reaction with an alkyl halide, triflate, or tosylate in the presence of a base such as sodium or potassium terbutoxide. Alternatively the indole can be deprotonated by strong base such as sodium hydride or n-butyl lithium and then the anion reacted with the alkyl alkyl halide, triflate, or tosylate. See reaction depicted below.

The indole can also be arylated as depicted in Formula IIIg″ via nucleophilic aromatic substitution by reaction with an aryl fluoride in a suitable solvent such as tetrahydrofuran or dimethylformamide.

The benzyl protecting group can be removed by palladium hydrogenation conditions or with a strong acid. See reaction depicted below, where Formula IIIg refers to an indole substituted with any $R^4$ as described herein, and the deprotected product is shown in Formula IIIh.

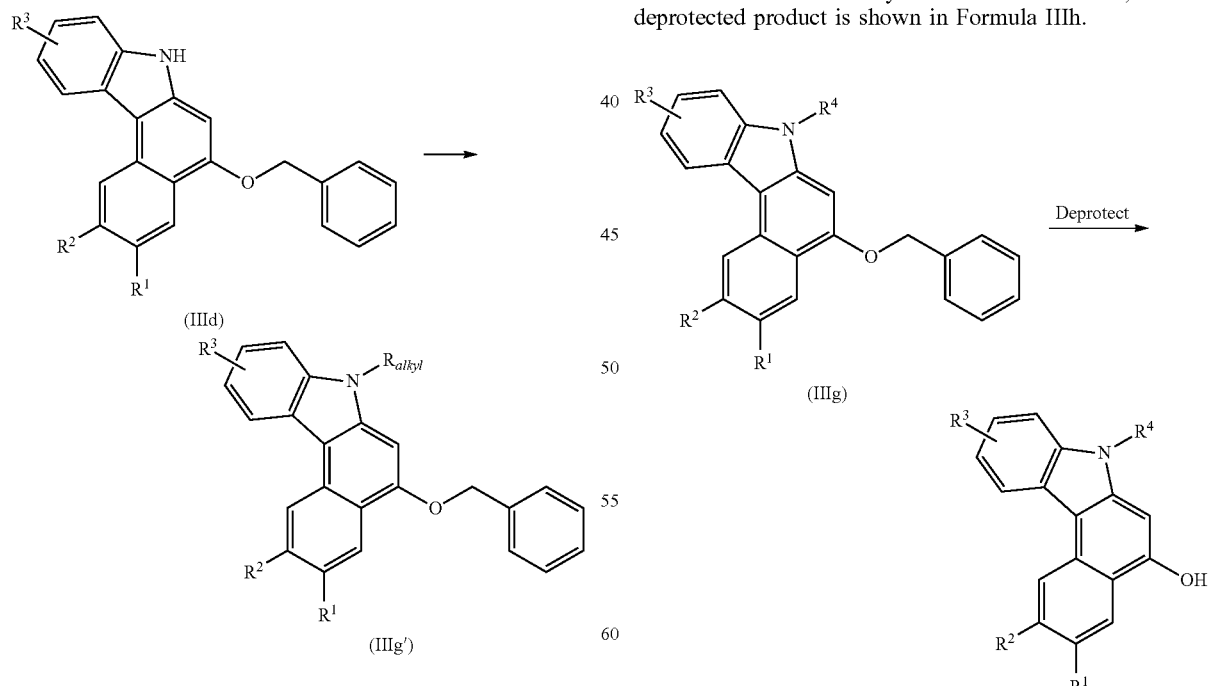

The indole group can be arylated, as depicted in Formula IIIg″, by cross coupling reactions with transition metal catalysts and aryl halides. Ullmann coupling methodology with a copper catalyst is common method to perform this transformation. See reaction depicted below.

The indole-fused naphthol depicted in Formula IIIh can then be reacted with aryl propargyl alcohols under acidic conditions to yield indole-fused naphthopyrans, as depicted in Formula Ia. See reaction depicted below.

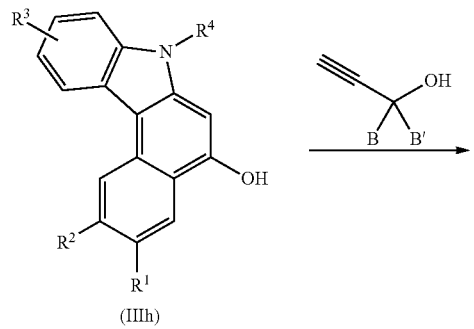

(IIIh)

(Ia)

As previously mentioned and illustrated in the examples below, the compounds useful in the articles of the present invention exhibit A band to B band absorption ratios of greater than 3:1 and in some cases greater than 6:1, such as 3 to 7:1, such as 3 to 6.5:1, such as 3 to 6.4:1, or such as 3.45 to 6.4:1.

The articles of the present invention can be photochromic articles that include one or more of the indolenaphthopyran compounds as represented by Formula (I) or (Ia). The photochromic articles can be prepared by art-recognized methods, such as by imbibition methods, cast-in-place methods, coating methods, in-mold coating methods, over-mold methods, and lamination methods.

For example, the photochromic articles can be selected from ophthalmic articles, display articles, windows, mirrors, active liquid crystal cell articles, and passive liquid crystal cell articles.

For example, the photochromic articles of the present invention can be ophthalmic articles, and the ophthalmic articles can be selected from corrective lenses, non-corrective lenses, contact lenses, intra-ocular lenses, magnifying lenses, protective lenses, and visors.

For example, the photochromic articles of the present invention can be display articles, and the display articles can be selected from screens, monitors, and security elements.

Such photochromic articles, e.g., photochromic lenses, can transition from a first unactivated state (e.g., colorless and non-blue blocking state) to a second activated state (e.g., colored and blue-blocking state) upon exposure to actinic radiation. The articles can revert back to the first unactivated (and clear or colorless) state upon removal of the actinic radiation source. Thus, the photochromic articles according to the present invention provide enhanced protection from health risks associated with blue light exposure during outdoor activity, while maintaining acceptable aesthetics indoors.

The present invention is more particularly described in the following examples, which are intended as illustrative only, since numerous modifications and variations therein will be apparent to those skilled in the art.

EXAMPLES

Preparation of the indolenaphthopyran compounds used in the preparation of the articles of the present invention is described below with reference to the following Examples 1 through 11, and Examples 1A and 2A. Unless indicated otherwise, structures of the compounds were confirmed by mass spectroscopy.

Part 1: Synthesis of Compounds

Example 1

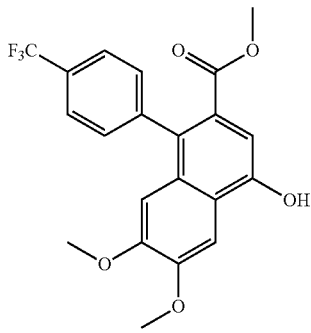 [SMILES: COC(=O)c1cc(O)c2cc(OC)c(OC)cc2c1-c1ccc(C(F)(F)F)cc1]

Step 1

Methyl 4-acetoxy-6,7-dimethoxy-1-(4-(trifluoromethyl) phenyl)-2-naphthoate (50 g, 131 mmol) was dispersed in methanol (200 ml) with stirring. Concentrated hydrochloric acid (8 ml) was added and the reaction mixture was heated to reflux for 4 hours. Once cool, the reaction mixture was concentrated to half the original volume and the product precipitated upon standing. The product was collected and dried under vacuum to give 41 g (90% yield) of a colorless powder.

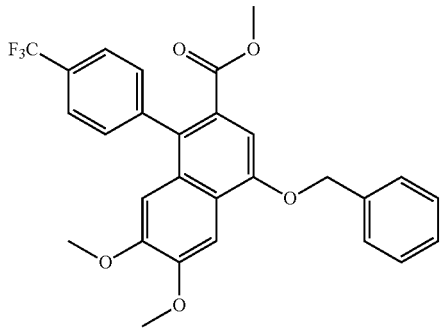 [SMILES: COC(=O)c1cc(OCc2ccccc2)c2cc(OC)c(OC)cc2c1-c1ccc(C(F)(F)F)cc1]

Step 2

While stirring under nitrogen, the product from Step 1 (41 g, 101 mmol) was dissolved in anhydrous dimethylformamide (200 ml) and potassium carbonate (28.0 g, 202 mmol) was added followed by benzyl chloride (15.3 g, 121 mmol). The reaction mixture was heated to 70° C. for 5 hours and let stir overnight at room temperature. A precipitate began to form and the reaction mixture was poured into ice water (1.0 L) with stirring. The precipitate was collected and dried under vacuum to give 49.44 g (99% yield) of a colorless solid.

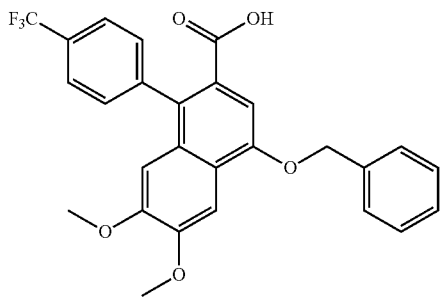 [SMILES: COc1cc2c(OCc3ccccc3)cc(C(=O)O)c(-c3ccc(C(F)(F)F)cc3)c2cc1OC]

Step 3

The product from Step 2 (49.4 g, 99.5 mmol) was suspended in 2-propanol (150 ml) with stirring. Sodium hydroxide solution (10% w/w in water, 150 ml) was added and the reaction mixture was heated to reflux for 16 hours. Once cool, the reaction mixture was poured into ice water (1.0 L) to form a colorless precipitate. The powder was collected and dried under vacuum to give 46.71 g (97% yield).

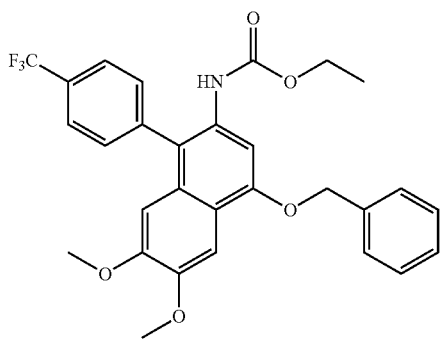 [SMILES: CCOC(=O)Nc1cc(OCc2ccccc2)c2cc(OC)c(OC)cc2c1-c1ccc(C(F)(F)F)cc1]

Step 4

While stirring under nitrogen, the product from Step 3 (46.7 g, 96.8 mmol) was suspended in anhydrous toluene (300 ml). Triethylamine (25.5 g, 252 mmol) and absolute ethanol (25 ml) were added dissolving the suspension. Diphenylphosphoryl azide (40 g, 145 mmol) was added portion-wise and the reaction was heated to reflux for 3 hours. Once cool, the reaction mixture was taken up in 200 ml of ethyl acetate, washed with water (4×300 ml), dried with sodium sulfate and concentrated under reduced pressure to give an off-white solid (50 g, 98% yield).

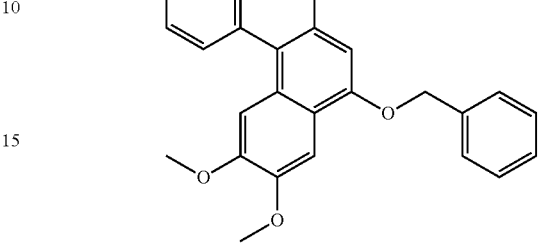

Step 5

The product from Step 4 (50.0 g, 95.1 mmol) was dispersed in a solution of ethanol (200 ml) and water (220 ml) with sodium hydroxide (19.2 g, 48.0 mmol) with stirring. The reaction mixture was heated to reflux for 4 hours. Once cool, the reaction mixture was poured into ice water (1.0 L) and a colorless precipitate was formed. The powder was collected and dried under vacuum to give 41.81 g (97% yield).

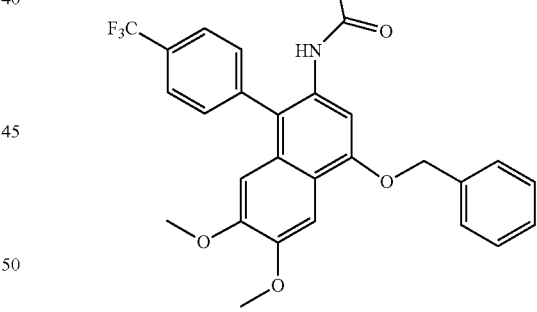

Step 6

While stirring under nitrogen, the product from Step 5 (41.81 g, 92.2 mmol) was taken up in dichloromethane (250 ml). Picolinic acid (17.0 g, 138.3 mmol) and 4-(dimethylamino)pyridine (1.13 g, 9.20 mmol) were added followed by N,N'-dicyclohexylcarbodiimide (22.8 g, 110.6 mmol). The reaction mixture was allowed to stir at room temperature for 4 hours. The reaction mixture was filtered and concentrated under reduced pressure to give a reddish solid. The material was washed with methanol, collected and dried under vacuum to give 50.9 g, (99% yield) of an off-white powder.

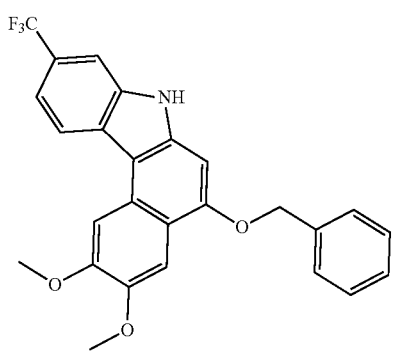 [SMILES: COc1cc2c(OCc3ccccc3)cc3[nH]c4cc(C(F)(F)F)ccc4c3c2cc1OC]

Step 7

While stirring under nitrogen, the product from Step 6 (50.9 g, 91.1 mmol) was dissolved in anhydrous dimethylformamaide (100 ml) and to this was added copper (II) acetate (33.1 g, 182.2 mmol) and glacial acetic acid (5.47 g, 91.1 mmol). The reaction mixture was heated to 150° C. for 20 hours to give 66% conversion of the starting material to product determined by high performance liquid chromatography. The reaction mixture was filtered over a celite pad and the pad was washed with 500 ml of ethyl acetate. The filtrate was added to separatory funnel with water (1.0 L) containing ethylenediamine (10 ml) and the layers were separated. The organic layer was washed with water (3×300 ml), dried with sodium sulfate and concentrated under reduced pressure to give an off-white solid. The material was subjected to a second iteration of the reaction conditions and same isolation procedures. The resulting solid was washed twice with methanol (300 ml) to give an off-white powder (37.44 g 91% yield). The product indole core, 5-(benzyloxy)-2,3-dimethoxy-9-(trifluoromethyl)-7H-benzo[c]carbazole, was confirmed by $^1$H NMR and mass spectroscopy.

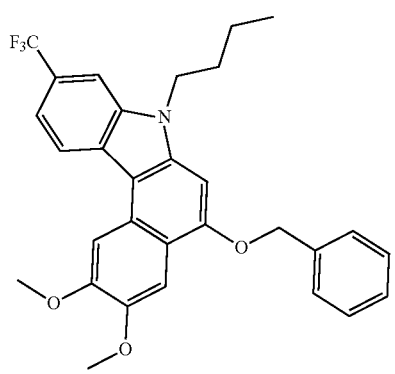 [SMILES: CCCCn1c2cc(C(F)(F)F)ccc2c2c3cc(OC)c(OC)cc3c(OCc3ccccc3)cc21]

Step 8

While stirring under nitrogen, the indole core from Step 7 (5.0 g, 11.1 mmol) was dissolved in anhydrous dimethylformamide (40 ml) and sodium hydride (0.8 g, 33.2 mmol) was added slowly. After 15 minutes, iodobutane (2.25 g, 12.2 mmol) was added and the reaction mixture was stirred at room temperature for 30 minutes. The reaction mixture was taken up in ethyl acetate (200 ml) and washed with water (3×200 ml). The organic layer was dried with sodium sulfate and concentrated under reduced pressure onto silica gel. Chromatography (silica gel, 0-50% dichloromethane in hexanes) yielded the product as a colorless solid (3.4 g, 60% yield).

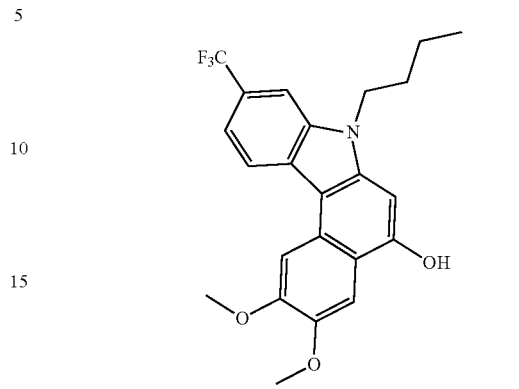

Step 9

While stirring under nitrogen, the product from Step 8 (1.50 g, 3.0 mmol) was combined with ammonium formate (0.75 g, 11.84 mmol) and palladium on carbon (Aldrich #768243, 5% loading on wet support, Degussa type E1003 U/W) in dimethylformamide (20 ml). The reaction mixture was heated to 85° C. for 2 hours. Once cool, the reaction mixture was filtered over a pad of celite and the pad was washed with ethyl acetate (250 ml). The filtrate was washed with water (3×300 ml), dried with sodium sulfate and concentrated under reduced pressure to give an off-white solid that was used without further purification.

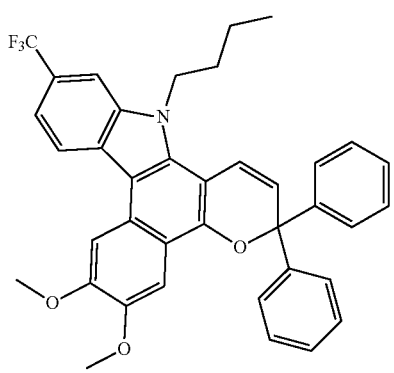 [SMILES: CCCCn1c2cc(C(F)(F)F)ccc2c2c3cc(OC)c(OC)cc3c3c(c21)C=CC(c1ccccc1)(c1ccccc1)O3]

Step 10

While stirring under nitrogen, the product from Step 9 (0.62 g, 1.48 mmol) was combined with 1,1-diphenylprop-2-yn-1-ol (0.37 g, 1.78 mmol) in toluene (25 ml) and heated to 75° C. p-Toluenesulfonic acid (5-10 mg) was added and the reaction mixture was heated to reflux for 2 hours. Once cool the reaction mixture was taken up in ethyl acetate (25 ml), washed with saturated sodium bicarbonate solution (25 ml) and water (2×50 ml). The organic layer was dried with sodium sulfate and concentrated under reduced pressure to give a dark oil. The product was recrystallized twice from methyl tert-butylether, tetrahydrofuran and methanol to give Example 1 as a light yellow powder (0.48 g, 54% yield) and confirmed by mass spectroscopy.

Example 2

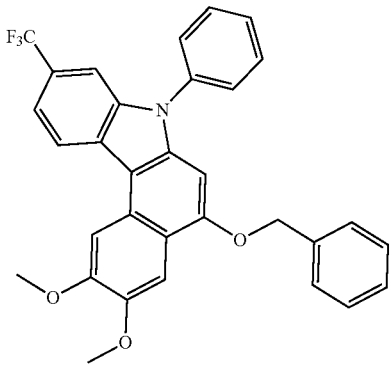 [SMILES: COc1cc2c(OCc3ccccc3)cc3c(c2cc1OC)c1ccc(C(F)(F)F)cc1n3-c1ccccc1]

Step 1

While stirring under nitrogen, the indole core prepared in Example 1, Step 7 (3.0 g, 6.64 mmol) was combined with bromobenzene (4.2 g, 26.6 mmol), copper iodide (0.63 g, 3.32 mmol), potassium carbonate (1.82 g, 13.2 mmol), 1,10-phenanthroline (0.24 g, 1.30 mmol) and dibenzo-18-crown-6-ether (0.24 g, 0.70 mmol) in anhydrous dimethylformamide (30 ml). The reaction mixture was heated to 150° C. for 5 hours. Once cool, the reaction mixture was taken up in ethyl acetate (250 ml) and washed initially with water (200 ml) with ethylene diamine (10 ml) followed by water (2×250 ml). The organic layer was dried with sodium sulfate and concentrated under reduced pressure to give a brown solid. The product was recrystallized twice from methyl-tert-butylether, tetrahydrofuran and methanol to give an off-white powder (3.20 g, 910% yield).

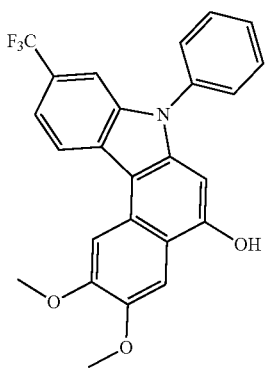 [SMILES: COc1cc2c(O)cc3c(c2cc1OC)c1ccc(C(F)(F)F)cc1n3-c1ccccc1]

Step 2

The product from Step 1 (1.20 g, 2.27 mmol) was treated to the conditions of Example 1, Step 9 to give an off-white solid that was used without further purification.

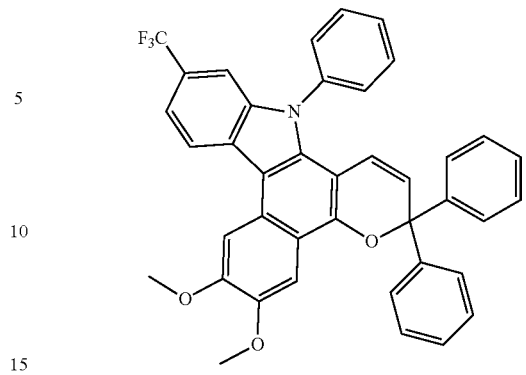

Step 3

The product from Step 2 was treated to conditions of Example 1, Step 10 to give a yellow powder (1.12 g, 79% yield) that was confirmed by mass spectroscopy.

Examples 3-6

Additional photochromic dyes were prepared according to Example 2 and are summarized in Table 1. For each example, an appropriate substituted phenyl bromide was used in place of bromobenzene in Example 2, Step 1 indicated in the N-Coupling Component column in Table 1. As well an appropriate substituted 1,1-diphenylprop-2-yn-1-ol ("propargyl alcohol") was used in Example 2, Step 3 indicated in the Propargyl Alcohol column in Table 1. Structures were confirmed by mass spectroscopy.

Example 7

Example 7 was prepared in the same manner as Example 1 except that methyl 4-acetoxy-6,7-dimethoxy-1-(4-(trifluoromethyl)phenyl)-2-naphthoate of Example 1, Step 1 was replaced with methyl 4-acetoxy-6,7-dimethoxy-1-phenyl-2-naphthoate and 1,1-diphenylprop-2-yn-1-ol of Example 1, Step 10 was replaced with 1-(4-methoxyphenyl)-1-phenyl-prop2-yn-1-ol. Summarized in Table 1 and the different core is indicated in the Indole Core column.

Example 8

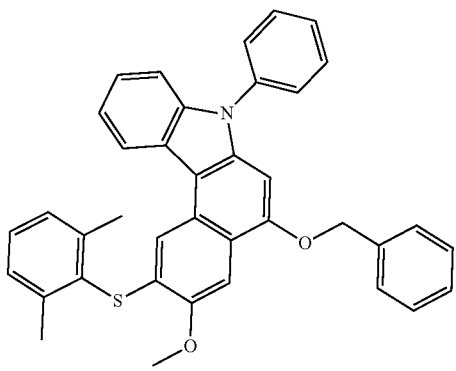 [SMILES: COc1cc2c(OCc3ccccc3)cc3c(c2cc1Sc1c(C)cccc1C)c1ccccc1n3-c1ccccc1]

Step 1

The initial intermediate was prepared according to the conditions of Example 1 and 2 except that methyl 4-acetoxy-6,7-dimethoxy-1-(4-(trifluoromethyl)phenyl)-2-naphthoate was replaced by methyl 4-acetoxy-7-((2,6-diemthylphenyl)thio)-6-methoxy-1-phenyl-2-naphthoate and summarized in Table 1.

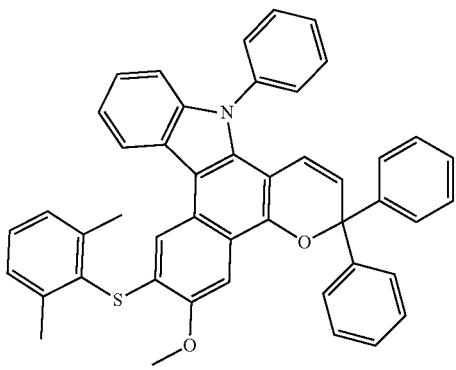 [SMILES: COc1cc2c3c(c4c(c2cc1Sc1c(C)cccc1C)c1ccccc1n4-c1ccccc1)C=CC(c1ccccc1)(c1ccccc1)O3]

Step 2

While stirring under nitrogen, the product of Step 1 (1.46 g, 2.58 mmol) was combined with p-toluenesulfonic acid (0.45 g, 2.58 mmol) in toluene (30 ml) and heated to 85° C. for 1 hour. Once cool, the reaction mixture was washed with water (2×75 ml), dried with sodium sulfate and concentrated under reduced pressure to give a yellow solid (1:2 mixture of product to byproduct). The solid was suspended in toluene (20 ml) and 1,1-diphenylprop-2-yn-1-ol (0.36 g, 1.73 mmol) was added. The reaction mixture was heated towards reflux and p-toluenesulfonic acid (5-10 mg) was added. After heating the reaction mixture at reflux for 1 hour, the reaction mixture was allowed to cool and concentrated under reduced pressure onto silica gel. Chromatography (silica gel, 0-50% dichloromethane in hexanes) yielded a yellow solid. Recrystallization from methyl tert-butylether, tetrahydrofuran and methanol gave a light yellow powder (0.23 g, 44% yield based on mixture) that was confirmed by mass spectroscopy.

Example 9

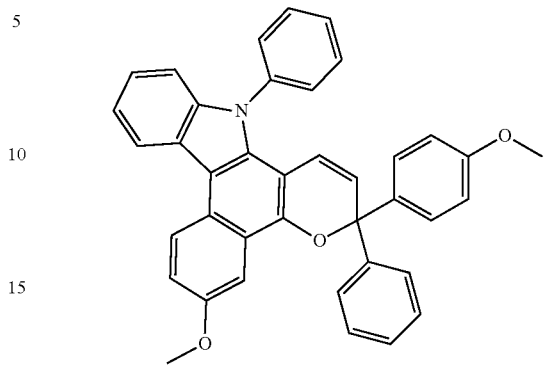

Example 9 was prepared according to the conditions of Example 1 and 2 except that methyl 4-acetoxy-6,7-dimethoxy-1-(4-(trifluoromethyl)phenyl)-2-naphthoate was replaced by methyl 4-acetoxy-6-methoxy-1-phenyl-2-naphthoate and summarized in Table 1.

Example 10

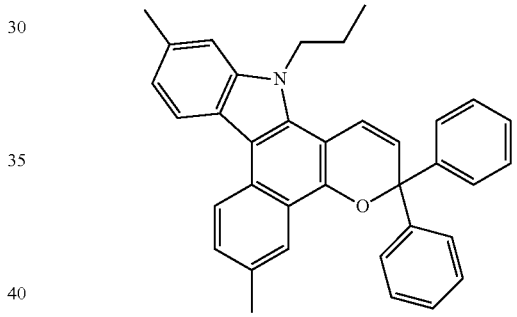

Example 10 was prepared according to the conditions of Example 1 except that methyl 4-acetoxy-6,7-dimethoxy-1-(4-(trifluoromethyl)phenyl)-2-naphthoate was replaced by methyl 4-acetoxy-6-methyl-1-(p-tolyl)-2-naphthoate and summarized in Table 1.

Example 11

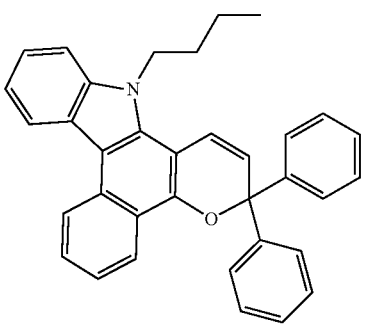 [SMILES: CCCCn1c2ccccc2c2c3ccccc3c3c(c21)C=CC(c1ccccc1)(c1ccccc1)O3]

Example 11 was prepared according to the conditions of Example 1 except that methyl 4-acetoxy-6,7-dimethoxy-1-

(4-(trifluoromethyl)phenyl)-2-naphthoate was replaced by methyl 4-acetoxy-1-phenyl-2-naphthoate and summarized in Table 1.

Examples 1A and 2A were prepared as described below and summarized in the following Table 2. Unless otherwise indicated, resulting product structures were confirmed by mass spectroscopy.

Example 1A

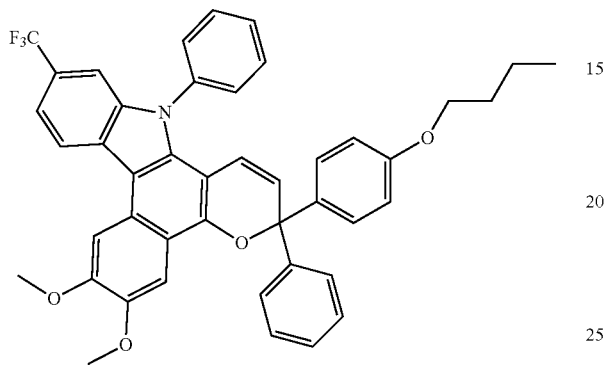

Step 1

While stirring under nitrogen, the product of Example 2, Step 2 (1.27 g, 2.90 mmol) was combined with 1-(4-butoxyphenol)-1-phenylprop-2-yn-1-ol (0.37 g, 1.78 mmol) in toluene (25 ml) and heated to 75° C. p-Toluenesulfonic acid (5-10 mg) was added and the reaction mixture was heated to reflux for 3 hours. Once cool the reaction mixture was taken up in ethyl acetate (200 ml), washed with saturated sodium bicarbonate solution (100 ml) and water (2×100 ml). The organic layer was dried with sodium sulfate and concentrated under reduced pressure onto silica gel. Chromatography (silica gel, 0-70% ethyl acetate in hexanes) yielded an off-white powder. The product was recrystallized twice from methyl tert-butylether, tetrahydrofuran and methanol to give a colorless powder (1.21 g, 60% yield) and confirmed by $^1$H NMR spectroscopy and mass spectroscopy.

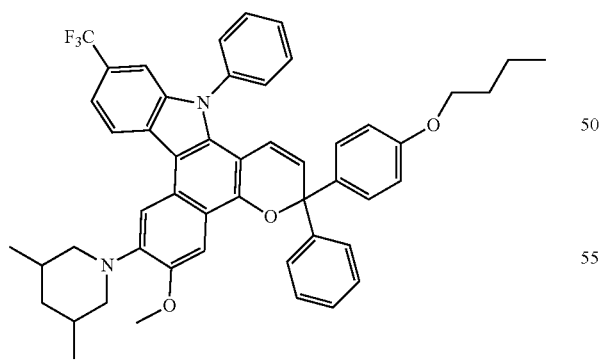

Step 2

While stirring under nitrogen, dimethylpiperdine (0.33 g, 2.90 mmol) was added to anhydrous tetrahydrofuran (35 ml). n-butyllithium (2.5M in hexane, 1.2 ml) was added slowly and the mixture was allowed to stir at room temperature for 5 minutes. The product of Step 1 (0.5 g, 0.71 mmol) was added and the reaction mixture was allowed to stir for an additional 4 hours. The reaction mixture was poured into water (250 ml) and extracted with ethyl acetate (2×50 ml). The organic layers were dried with sodium sulfate and concentrated onto silica gel. Chromatography (silica gel, 0 to 50% dichloromethane in hexanes) yielded the product as an off-white solid (0.096 g, 20% yield) that was confirmed by mass spectroscopy.

Example 2A

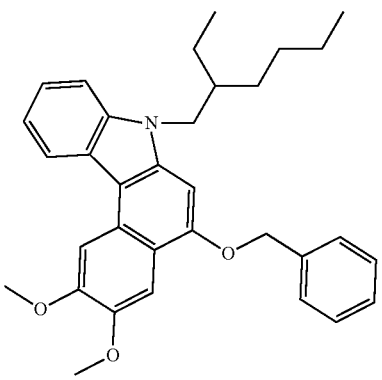 [SMILES: CCCCC(CC)Cn1c2ccccc2c2c3cc(OC)c(OC)cc3c(OCc3ccccc3)cc21]

Step 1

The indole core, 5-(benzyloxy)-2,3-dimethoxy-7H-benzo[c]carbazole from Example 7, was treated to conditions of Example 1, Step 8 with 1-bromo-2-ethylhexane instead of iodobutane.

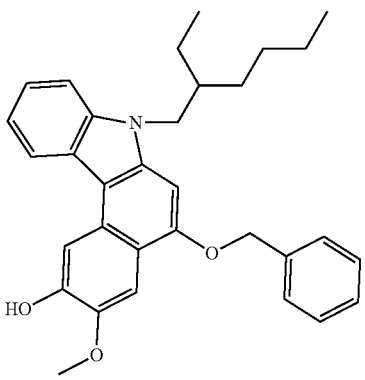 [SMILES: CCCCC(CC)Cn1c2ccccc2c2c3cc(O)c(OC)cc3c(OCc3ccccc3)cc21]

Step 2

While stirring under nitrogen, a methyl Grignard solution (1.4 M, 29.0 ml) was added slowly by syringe to dimethylpiperidine (4.93 g, 40.0 mmol) and the reaction mixture was allowed to stir for 10 minutes. The product from Step 1 (4.95 g, 10.0 mmol) was dissolved in anhydrous tetrahydrofuran (30 ml) and added dropwise over 10 minutes to the Grignard/dimethylpiperidine mixture. Once added, the reaction mixture was refluxed for 3 hours. Upon cooling, the reaction mixture as poured into a 1M HCl solution (75 ml) and the aqueous layer was extracted with ethyl acetate (3×150 ml). The organic layers were combined, dried with sodium sulfate and concentrated under reduced pressure onto silica. Chromatography (silica gel, 0-100% dichloromethane in hexanes) yielded a semi-solid

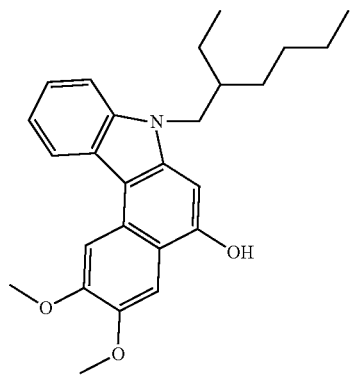 [SMILES: CCCCC(CC)Cn1c2ccccc2c2c3cc(OC)c(OC)cc3c(O)cc21]

Step 3

The product of Step 2 (2.17 g, 4.50 mmol) was treated to the conditions of Example 1, Step 9 to give a foam that was used without further purification.

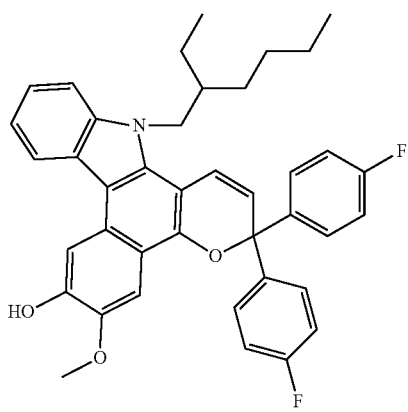 [SMILES: CCCCC(CC)Cn1c2ccccc2c2c3cc(O)c(OC)cc3c3c(c21)C=CC(c1ccc(F)cc1)(c1ccc(F)cc1)O3]

Step 4

While stirring under nitrogen, the product of Step 3 was combined with 1,1-bis(4-fluorophenyl)prop-2-yn-1-ol and dissolved in toluene (40 ml). The mixture was heated towards reflux and p-toluenesulfonic acid (10 mg) was added. The reaction mixture was heated at reflux for 5 hours until the conversion of the reaction was determined to be 60% by high performance liquid chromatography and once cool, concentrated onto silica gel. Chromatography (silica gel, 5-50% ethyl acetate in hexanes) yielded a brown/green glass (0.85 g, 30% yield).

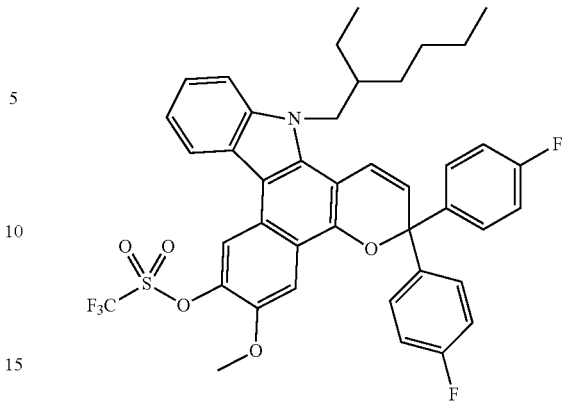

Step 5

While stirring under nitrogen, the product of Step 4 (0.85 g, 1.38 mmol) was dissolved in anhydrous dichloromethane (25 ml). Anhydrous pyridine (0.5 ml, 5.52 mmol) was added and the reaction mixture was cooled in an ice bath. Trifluoromethanesulfonic anhydride (0.51 g, 1.80 mmol) was added dropwise. After 30 minutes the reaction mixture was poured into water and the layers were separated. The aqueous layer was washed with dichloromethane (2×30 ml). The organic layers were combined, dried with sodium sulfate and concentrated under reduced pressure to give a brown/green glass (1.0 g, 97% yield).

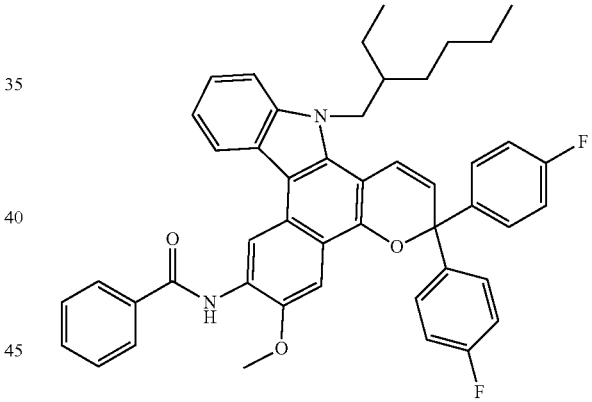

Step 6

The product from Step 5 (1.0 g, 1.33 mmol) was combined with benzamide (0.25 g, 2.0 mmol), cesium carbonate (1.80 g, 5.52 mmol) and 4,5-bis(diphenylphosphino)-9,9-dimethylxanthene (Xantphos) in toluene and ethanol solution (30 ml, 9:1 v/v) and sparged under nitrogen for 10 minutes. Tris(dibenzylideneacetone)dipalladium(0) (0.12 g, 0.13 mmol) was added and the reaction mixture was heated to reflux for 2 hours. The reaction mixture was taken up in ethyl acetate (100 ml), washed with water (2×100 ml), dried with sodium sulfate and concentrated onto silica gel. Chromatography (silica gel, 0-30% ethyl acetate in hexanes) yielded a brown solid. Recrystallization from methanol gave 0.38 g (40% yield) of a light yellow powder.

TABLE 1

Synthesis Summary

| Example | Structure | Indole Core | N-Coupling component | Yield[1] (%) | Propargyl Alcohol | Yield[2] (%) |
|---|---|---|---|---|---|---|
| 1 | (structure with butyl N-substituent, two phenyls, OMe groups, CF3) | (indole core with NH, OBn, two OMe, CF3) | 1-bromobutane | 60 | 1,1-diphenyl-2-propyn-1-ol | 54 |
| 2 | (structure with phenyl N-substituent, two phenyls, OMe groups, CF3) | (indole core with NH, OBn, two OMe, CF3) | bromobenzene | 91 | 1,1-diphenyl-2-propyn-1-ol | 79 |

TABLE 1-continued

Synthesis Summary

| Example | Structure | Indole Core | N-Coupling component | Yield[1] (%) | Propargyl Alcohol | Yield[2] (%) |
|---|---|---|---|---|---|---|
| 3 | 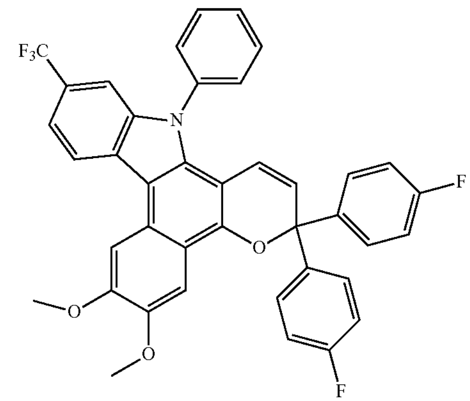 [SMILES: COc1cc2c3c(c4c(c2cc1OC)c1ccc(C(F)(F)F)cc1n4-c1ccccc1)C=CC(c1ccc(F)cc1)(c1ccc(F)cc1)O3] | | | 91 | | 63 |
| 4 | 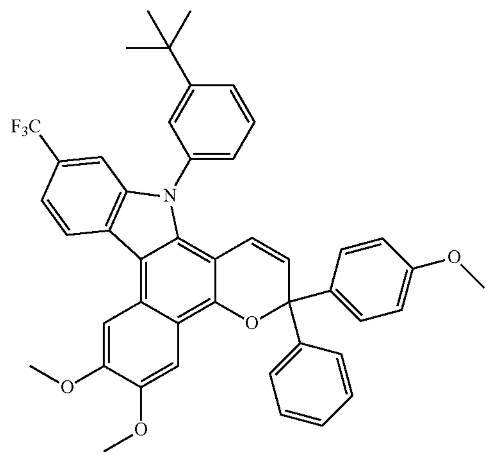 | | | 90 | | 52 |

TABLE 1-continued

Synthesis Summary

| Example | Structure | Indole Core | N-Coupling component | Yield[1] (%) | Propargyl Alcohol | Yield[2] (%) |
|---|---|---|---|---|---|---|
| 5 | 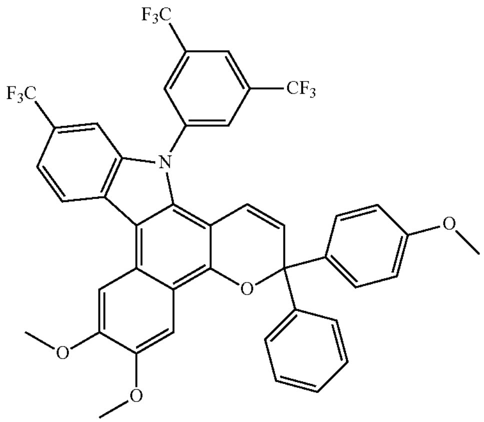 | | 3-bromo-5-(trifluoromethyl) substituted; 3,5-bis(CF₃) bromobenzene | 89 | 1-(4-methoxyphenyl)-1-phenylprop-2-yn-1-ol | 84 |
| 6 | 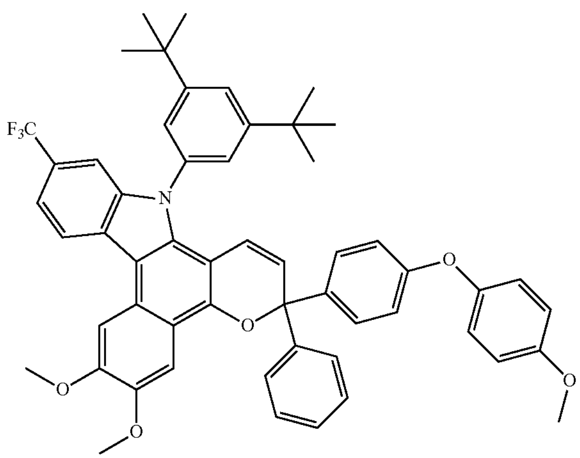 [SMILES: COc1ccc(Oc2ccc(C3(c4ccccc4)C=Cc4c(c5cc(OC)c(OC)cc5c5c6ccc(C(F)(F)F)cc6n(-c6cc(C(C)(C)C)cc(C(C)(C)C)c6)c45)O3)cc2)cc1] | | 1-bromo-3,5-di-tert-butylbenzene | 50 | 1-(4-(4-methoxyphenoxy)phenyl)-1-phenylprop-2-yn-1-ol | 74 |

TABLE 1-continued

Synthesis Summary

| Example | Structure | Indole Core | N-Coupling component | Yield[1] (%) | Propargyl Alcohol | Yield[2] (%) |
|---|---|---|---|---|---|---|
| 7 | [structure] | [structure] | [1-bromobutane] | 88 | [1-(4-methoxyphenyl)-1-phenyl-2-propyn-1-ol] | 18 |
| 8 | [structure] | [structure] | [bromobenzene] | 72 | [1,1-diphenyl-2-propyn-1-ol] | 44 |

TABLE 1-continued

Synthesis Summary

| Example | Structure | Indole Core | N-Coupling component | Yield[1] (%) | Propargyl Alcohol | Yield[2] (%) |
|---|---|---|---|---|---|---|
| 9 | 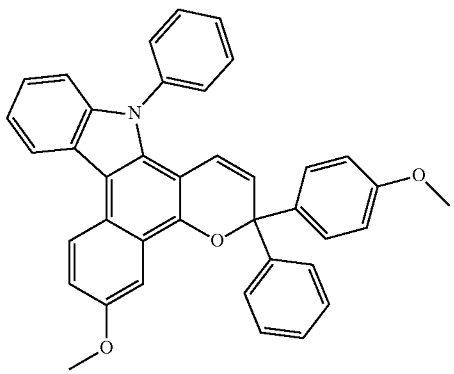 [SMILES: COc1ccc(C2(c3ccccc3)C=Cc3c(c4cc(OC)ccc4c4c5ccccc5n(-c5ccccc5)c34)O2)cc1] | | bromobenzene | 82 | 1-(4-methoxyphenyl)-1-phenyl-2-propyn-1-ol | 76 |
| 10 | 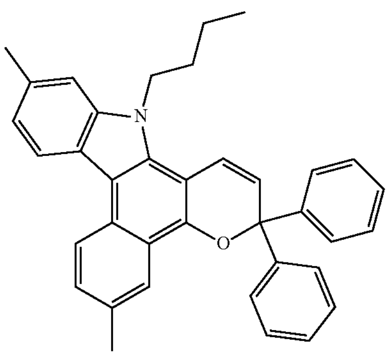 [SMILES: CCCCn1c2cc(C)ccc2c2c3ccc(C)cc3c3c(c21)C=CC(c1ccccc1)(c1ccccc1)O3] | | 1-bromobutane | 96 | 1,1-diphenyl-2-propyn-1-ol | 46 |

TABLE 1-continued

Synthesis Summary

| Example | Structure | Indole Core | N-Coupling component | Yield[1] (%) | Propargyl Alcohol | Yield[2] (%) |
|---|---|---|---|---|---|---|
| 11 | 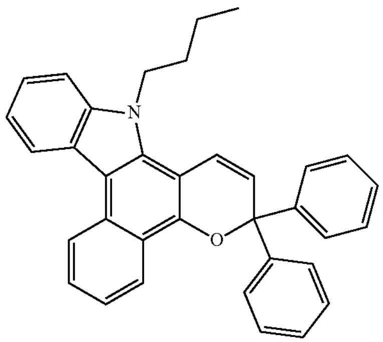 [SMILES: CCCCn1c2ccccc2c2c3ccccc3c3c(c21)C=CC(c1ccccc1)(c1ccccc1)O3] | | | 89 | | 53 |

[1] Yield corresponds to isolated intermediate.
[2] Yield corresponds to isolated dye compound.

TABLE 2

Experimental Summary

| Example | Structure | Indole Core |
|---------|-----------|-------------|
| 1A | 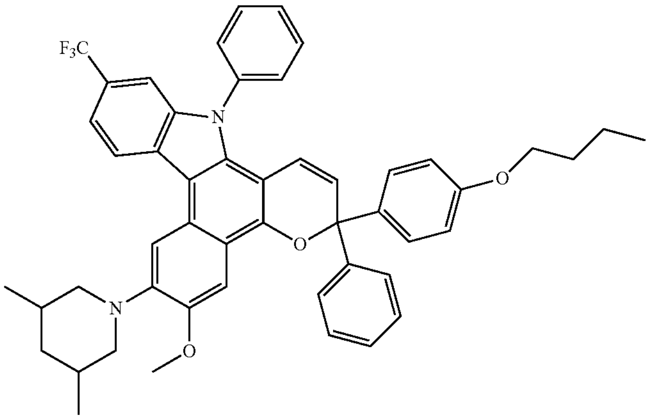 [SMILES: CCCCOc1ccc(C2(c3ccccc3)C=Cc3c(c4cc(OC)c(N5CC(C)CC(C)C5)cc4c4c5ccc(C(F)(F)F)cc5n(-c5ccccc5)c34)O2)cc1] | |
| 2A | 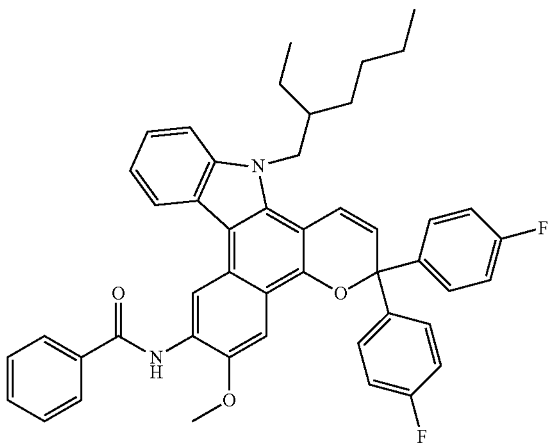 [SMILES: CCCCC(CC)Cn1c2ccccc2c2c3cc(NC(=O)c4ccccc4)c(OC)cc3c3c(c21)C=CC(c1ccc(F)cc1)(c1ccc(F)cc1)O3] | |

| Example | N-Coupling component | Propargyl Alcohol | Amination Component |
|---------|---------------------|-------------------|---------------------|
| 1A | | | |
| 2A | | | |

Part 2: Testing

Each of the photochromic dyes from Examples 1 through 11 and 1A and 2A, and each comparative example CE1 to CE4 were incorporated into a polyurethane coating system as described in U.S. Pat. No. 8,608,988 examples 1-3 at the same mol % and applied at the same coating thickness to 2"×2" test chips made from CR-39® monomer (PPG Industries, Inc.). All coated test chips were cured at 125° C. for 1 hour.

Each of the coated test chips (hereinafter "test samples") was conditioned by first being exposed to 365-nanometer ultraviolet light for 10 minutes at a distance of about 14 centimeters to activate the photochromic materials within the coating. The UVA (315 to 380 nm) irradiance at the test sample was measured with a LICOR® Model Li-1800 spectroradiometer and found to be 22.2 watts per square meter. Each of the test samples was then placed under a 500 watt, high intensity halogen lamp for 10 minutes at a distance of about 36 centimeters to bleach (inactivate) the photochromic materials. The illuminance at the test samples was measured with the LICOR® spectroradiometer and found to be 21.9 Klux. The test samples then were kept in a dark environment at room temperature (i.e., from 70 to 75° F., or 21 to 24° C.) for at least 1 hour prior to testing on an optical bench. Prior to optical bench measurement, the test samples were measured for ultraviolet absorbance at 390 nanometers.

Percent transmission for Examples 1 through 11, 1A and 2A, and for each comparative example CE1 through CE4 was determined using the CIE Y value in accordance with CIE 15: 2004 colorimetry using a D 65 illuminant and 100 observer. The a* and b* values as used herein in the specification and the claims refers to the a* and b* values measured in accordance with in accordance with CIE 15: 2004 space colorimetry, employing a D 65 illuminant and 10° observer, using the Hunter UltraScan Pro unit. Percent spectral blue light transmission (reported herein as $\tau_{SB}$) was determined in accordance with ISO 12311:2013(E), Subsection 7.4.

The BMP optical bench was fitted with two 150-watt ORIEL® Model #66057 Xenon arc lamps at right angles to each other. The light path from Lamp 1 was directed through a 3 mm SCFIOTT® KG-2 band-pass filter and appropriate neutral density filters that contributed to the required UV and partial visible light irradiance level. The light path from Lamp 2 was directed through a 3 mm SCFIOTT® KG-2 band-pass filter, a SCFIOTT® short band 400 nm cutoff filter and appropriate neutral density filters in order to provide supplemental visible light illuminance. A 2 inch×2 inch 50% polka dot beam splitter, at 450 to each lamp is used to mix the two beams. The combination of neutral density filters and voltage control of the Xenon arc lamp were used to adjust the intensity of the irradiance. Proprietary software i.e., BMPSoft version 2.1e was used on the BMP to control timing, irradiance, air cell and sample temperature, shuttering, filter selection and response measurement. A ZEISS® spectrophotometer, Model MCS 501, with fiber optic cables for light delivery through the test sample was used for response and color measurement. Photopic response measurements were collected on each test samples. The power output of the optical bench, i.e., the dosage of light that the test sample was exposed to, was adjusted to 6.7 Watts per square meter (W/m²) UVA, integrated from 315-380 nm and 50 Klux illuminance, integrated from 380-780 nm. Measurement of this power setpoint was made using an irradiance probe and the calibrated Zeiss spectrophotometer. The sample cell was fitted with a quartz window and self-centering sample holder. The temperature in the sample cell was controlled at 23° C. through the software with a modified Facis, Model FX-10, environment simulator. Measurement of the test sample's dynamic photochromic response and color measurements was made using the same Zeiss spectrophotometer, with fiber optic cables for light delivery from a tungsten halogen lamp and through the test sample. The collimated monitoring light beam from the fiber optic cable was maintained perpendicular to the test sample while passing through the sample and directed into a receiving fiber optic cable assembly attached to the spectrophotometer. The exact point of placement of the sample in the sample cell was where the activating xenon arc beam and the monitoring light beam intersected to form two concentric circles of light. The angle of incidence of the xenon arc beam at the sample placement point was =30° from perpendicular.

Response measurements, in terms of a change in optical density (ΔOD) from the unactivated or bleached state to the activated or colored state were determined by establishing the initial unactivated transmittance, opening the shutter from the Xenon lamp(s) and measuring the transmittance through activation at selected intervals of time. The change in optical density was determined according to the formula: $\Delta OD = \log(10)(\% Tb/\% Ta)$, where % Tb is the percent transmission in the bleached state, % Ta is the percent transmission in the activated state. The ΔOD at saturation is after 15 minutes of activation and the Fade Half Life ("T½") value is the time interval in seconds for the ΔOD of the activated form of the photochromic material in the coating to reach one half the fifteen minute ΔOD at 73.4° F. (23° C.), after removal of the activating light source.

Fatigue Testing:

Procedures for Fatigue Testing and results prior to initial performance testing were determined on an optical bench. The test samples were conditioned by exposing them to 365 nm ultraviolet light for 15 minutes at a distance of about 14 cm from the source in order to activate the photochromic molecules. The UVA irradiance at the test chip was measured with a Licor Model Li-1800 spectroradiometer and found to be 22.2 Watts per square meter. The test samples were then placed into an oven at 75° C. for 1 hour. The test samples then were exposed to room light for 3 hours. Finally, the test samples were then kept in a dark environment for at least 1 hour prior to testing in order to continue to fade back to a ground state prior to testing.

An optical bench fitted with a Schott 3 mm KG-2 band-pass filter, neutral density filter(s) and a Newport Model #67005 300-watt Xenon arc lamp with Model #69911 power supply in association with a Newport Model 689456 Digital Exposure/Timer was used to control the intensity of the irradiance beam utilized for activation of each coated test sample. A Uniblitz model #CS25S3ZMO high-speed shutter with model #VMM-D3 controller, and fused silica condensing lenses for activation beam collimation and focusing through a quartz water cell/sample holder for maintaining sample temperature in which each test sample to be tested was inserted. The temperature in the water cell was controlled with a pumped water circulation system in which the water passed through copper coils that were placed in the reservoir of a chiller unit. The water cell used to hold test samples contained fused silica sheets on the front and back facings in order to eliminate spectral change of the activation or monitoring light beams. The filtered water passing through the water cell was maintained at 100° F.±2° for photochromic testing before and after exposure to the Atlas Weatherometer.

A custom made broadband light source for monitoring response measurements was positioned in a perpendicular manner to a surface of the cell assembly. This broad beam light source is obtained by collecting and combining separately filtered light from a 100-Watt tungsten halogen lamp (controlled by a Lambda UP60-14 constant voltage power supply) with a split-end, bifurcated fiber optical cable to enhance the short wavelength light intensity. After passing through the test sample, this monitoring light was refocused into a 2-inch integrating sphere and fed to an Ocean Optics S2000 spectrophotometer by fiber optic cables. Ocean Optics SpectraSuite and proprietary software were used to measure response and control the operation of the optical bench.

An International Light Research Radiometer, Model IL-1700 with a detector system comprising a Model SED033 detector, B Filter and diffuser was used to verify the irradiance prior to testing. An adjusted value of 18.0 W/m² was used as the irradiance verification set point. The output display of the radiometer was corrected (factor values set) against a Licor 1800-02 Optical Calibration Calibrator in order to display values representing Watts per square meter UVA. Increasing or decreasing the current to the lamp through the controller and/or by adding or removing neutral density filters in the activation light path was done to make adjustments to the xenon lamp output. The test samples were exposed to activation light at 31° normal to the surface of the test sample.

The change in optical density (ΔOD) from the bleached first state to the colored second state was determined by establishing the initial transmission, opening the shutter from the Xenon lamp to provide ultraviolet radiation to change the test sample from the bleached first state to an activated second (i.e., colored) state and measuring the transmission in the activated state after typically 5 minutes of activation. The change in Optical density is calculated using the formula: ΔOD log(% Tb/% Ta), where % Tb is the percent transmission in the bleached first state, % Ta is the percent transmission in the activated state and the logarithm is to the base 10. This provided the $OD_{init}$.

An Atlas Ci4000 weatherometer was used for conducting the simulated solar radiation accelerated weathering. The test samples were exposed for a 1 hour dark cycle and then a 65 hour light cycle using a boro/boro silicate filtered Xenon arc lamp with an output of 0.25 Watts per square meter at 340 nm. The temperature in the weatherometer was maintained at 45° C. and the relative humidity was controlled at 70% humidity. The temperature of the black panel was maintained at 55° C.

After the test samples underwent this UV exposure fatigue cycle, the samples were preconditioned as described above and measured on the optical bench to obtain the final $\Delta OD_{final}$ under the same conditions as described for the initial testing.

The percent fatigue was determined by measuring the difference between the change in optical density (ΔOD) of the test sample before and after accelerated weathering according to the formula: % Fatigue=$(\Delta OD_{init}-\Delta OD_{final}/\Delta OD_{init})\times 100$.

The ΔOD at saturation is after 15 minutes of activation and the Fade Half Life ("T½") value is the time interval in seconds for the ΔOD of the activated form of the photochromic-dichroic material in the coating to reach one half the fifteen-minute ΔOD at 73.4° F. (23° C.), after removal of the activating light source.

Two absorption maxima ΔOD are observed for the indolenaphthopyran compounds of the present invention at full activation. Wavelength A ("λ A") is the wavelength with the maximum ΔOD between 420-500 nm and Wavelength B ("λ B") is the wavelength with maximum ΔOD between 500-650 nm. The A band to B band absorption ratio ("A-B ratio") is calculated by the formula:

A-B Ratio=max ΔOD wavelength A/max ΔOD wavelength A

Testing results are presented in Table 3 below.

TABLE 3

| Ex. # | Structure | 1st state % T | 1st state b* | 2nd state % T | 2nd state b* | Fade Half Life T½ (sec) | $\tau_{SB}$ (%) 1st state | $\tau_{SB}$ (%) 2nd state | Fatigue % OD Loss |
|---|---|---|---|---|---|---|---|---|---|
| 1 | 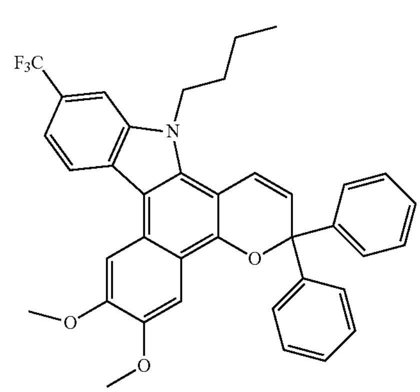 [SMILES: CCCCn1c2cc(C(F)(F)F)ccc2c2c3cc(OC)c(OC)cc3c3c(c21)C=CC(c1ccccc1)(c1ccccc1)O3] | 90.2 | 5.9 | 60.0 | 56.4 | 68 | 74.7 | 16.4 | 10.8 |

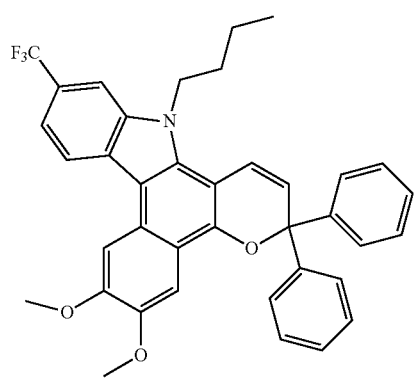

TABLE 3-continued

| Ex. # | Structure | 1st state %T | 1st state b* | 2nd state %T | 2nd state b* | Fade Half Life T½ (sec) | τ$_{SB}$ (%) 1st state | τ$_{SB}$ (%) 2nd state | Fatigue % OD Loss |
|---|---|---|---|---|---|---|---|---|---|
| 2 | 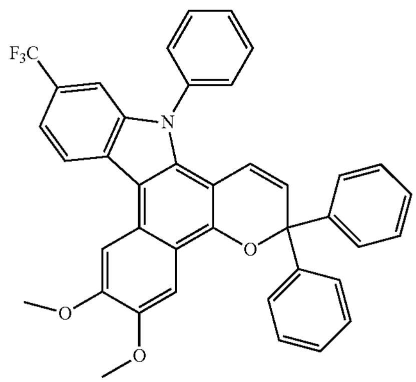 [SMILES: COc1cc2c3c(c4c(c2cc1OC)c1ccc(C(F)(F)F)cc1n4-c1ccccc1)C=CC(c1ccccc1)(c1ccccc1)O3] | 91.1 | 3.6 | 60.5 | 53.6 | 39 | 86.5 | 19 | 10.0 |
| 3 | 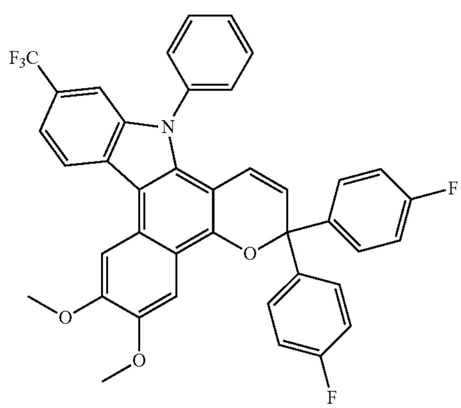 [SMILES: COc1cc2c3c(c4c(c2cc1OC)c1ccc(C(F)(F)F)cc1n4-c1ccccc1)C=CC(c1ccc(F)cc1)(c1ccc(F)cc1)O3] | 90.0 | 5.2 | 61.7 | 53.8 | 36 | 83.6 | 19.5 | 10.7 |
| 4 | 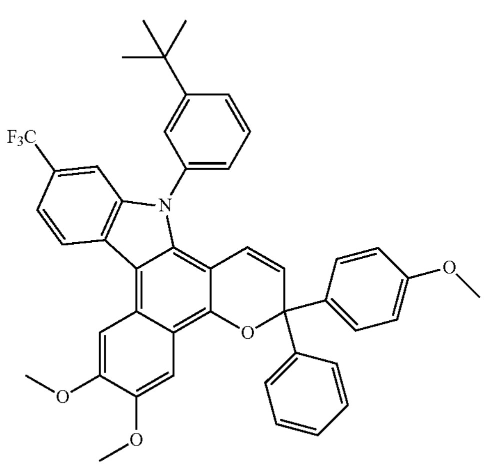 | 89.0 | 5.5 | 42.3 | 58.6 | 41 | 81.7 | 9.7 | 2.4 |

TABLE 3-continued

| Ex. # | Structure | 1st state % T | 1st state b* | 2nd state % T | 2nd state b* | Fade Half Life T½ (sec) | τ_SB (%) 1st state | τ_SB (%) 2nd state | Fatigue % OD Loss |
|---|---|---|---|---|---|---|---|---|---|
| 5 | 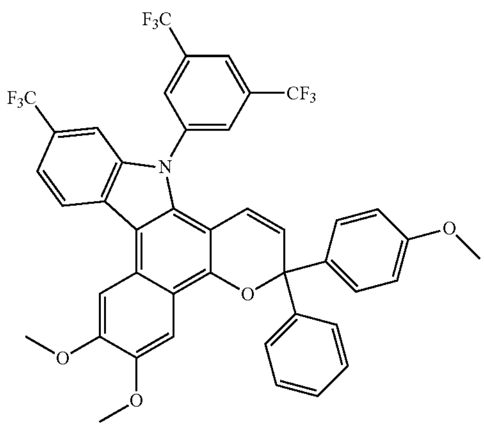 | 89.4 | 4.0 | 47.8 | 48.2 | 31 | 83.9 | 16.2 | 6.0 |
| 6 | 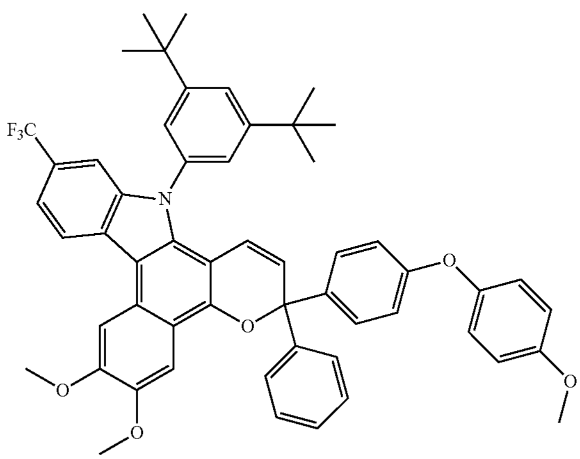 [SMILES: COc1ccc(Oc2ccc(C3(c4ccccc4)C=Cc4c(c5cc(OC)c(OC)cc5c5c6ccc(C(F)(F)F)cc6n(-c6cc(C(C)(C)C)cc(C(C)(C)C)c6)c45)O3)cc2)cc1] | 90.2 | 3.5 | 48.8 | 52.5 | 75 | 71.2 | 12.2 | 7.2 |
| 7 | 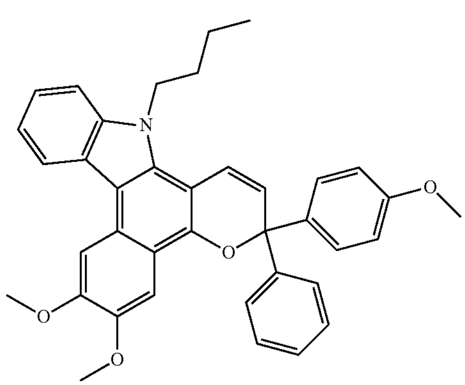 | 86.4 | 12.6 | 45.3 | 71.6 | 67 | 66.0 | 6.5 | 4.0 |

TABLE 3-continued

| Ex. # | Structure | 1st state % T | 1st state b* | 2nd state % T | 2nd state b* | Fade Half Life T½ (sec) | τSB (%) 1st state | τSB (%) 2nd state | Fatigue % OD Loss |
|---|---|---|---|---|---|---|---|---|---|
| 8 | 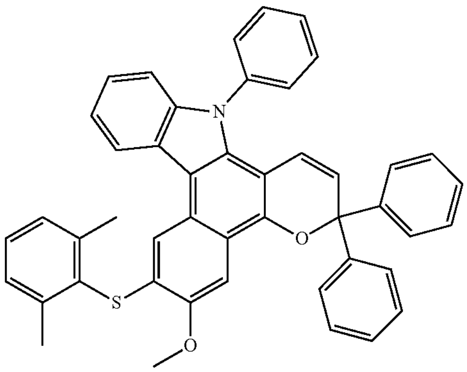 [SMILES: COc1cc2c3c(c4c(c2cc1Sc1c(C)cccc1C)c1ccccc1n4-c1ccccc1)C=CC(c1ccccc1)(c1ccccc1)O3] | 89.4 | 8.7 | 47.5 | 69.8 | 68 | 70.2 | 6.9 | 9.6 |
| 9 | 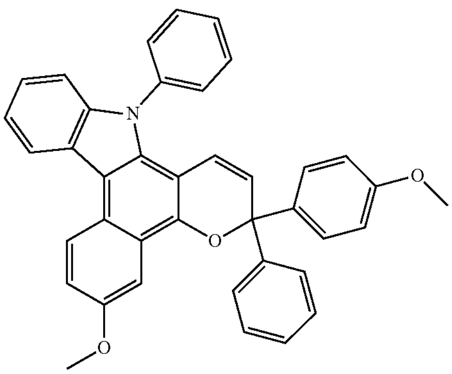 [SMILES: COc1ccc(C2(c3ccccc3)C=Cc3c(c4cc(OC)ccc4c4c5ccccc5n(-c5ccccc5)c34)O2)cc1] | 88.0 | 10.4 | 39.0 | 41.8 | 25 | 70.5 | 13.6 | 4.9 |
| 10 | 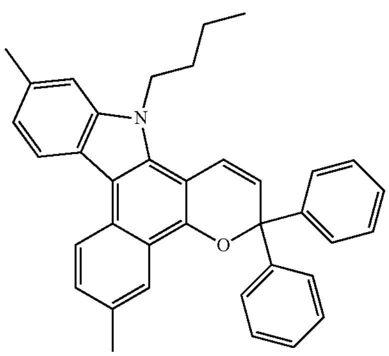 [SMILES: CCCCn1c2cc(C)ccc2c2c3ccc(C)cc3c3c(c21)C=CC(c1ccccc1)(c1ccccc1)O3] | 89.6 | 8.2 | 35.0 | 38.4 | 79 | 76.0 | 13.0 | 15.4 |
| 11 | 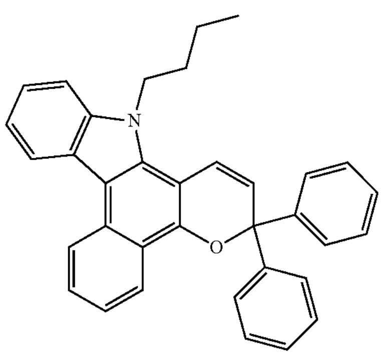 [SMILES: CCCCn1c2ccccc2c2c3ccccc3c3c(c21)C=CC(c1ccccc1)(c1ccccc1)O3] | 90.7 | 4.2 | 39.2 | 33.2 | 60 | 81 | 17.8 | 11 |

TABLE 3-continued

| | | 1st state | | 2nd state | | Fade Half Life T½ | $\tau_{SB}$ (%) | | Fatigue |
|---|---|---|---|---|---|---|---|---|---|
| | | | | | | | 1st | 2nd | |
| Ex. # | Structure | % T | b* | % T | b* | (sec) | state | state | % OD Loss |
| 1A | | 83.8 | 14.0 | 42.7 | 62.7 | 27 | 64.6 | 8.5 | 3.5 |
| 1B | | 90.5 | 14.1 | 52.3 | 70.4 | 66 | 68.5 | 8.5 | — |
| CE1 | | 89.8 | 1.7 | 14.2 | 25.2 | 144 | 87.2 | 4.8 | 5.4 |

TABLE 3-continued

| Ex. # | Structure | 1st state % T | 1st state b* | 2nd state % T | 2nd state b* | Fade Half Life T½ (sec) | τ_SB (%) 1st state | τ_SB (%) 2nd state | Fatigue % OD Loss |
|---|---|---|---|---|---|---|---|---|---|
| CE2 | 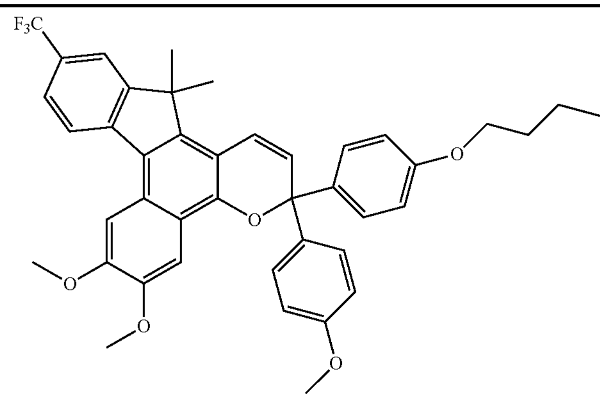 | 90.2 | 1.4 | 28.4 | 22.8 | 53 | 88.7 | 17.1 | 10.9 |
| CE3 | 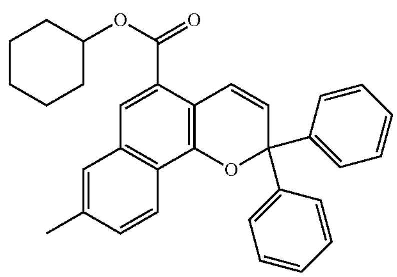 [SMILES: Cc1ccc2c3c(c(C(=O)OC4CCCCC4)cc2c1)C=CC(c1ccccc1)(c1ccccc1)O3] | 91.1 | 0.9 | 71.6 | 35.1 | 30 | 90.2 | 38.2 | 92.8 |
| CE4 | 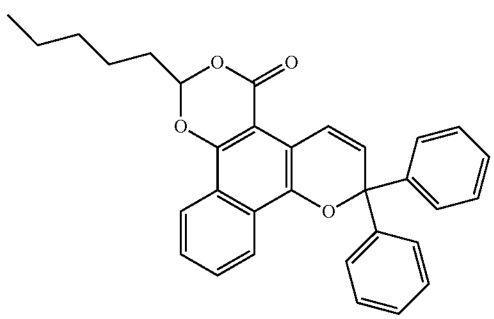 [SMILES: CCCCCC1OC(=O)c2c3c(c4ccccc4c2O1)OC(c1ccccc1)(c1ccccc1)C=C3] | 90.4 | 7.4 | 60.3 | 85.2 | 184 | 78.4 | 7.4 | 83.5 |

The data presented in Table 3 above illustrate that the photochromic indolenaphthopyran compounds used to prepare the articles of the present invention provide articles which provide excellent (low) blue light transmission in the second state as reported as $\tau_{SB}$, while maintaining very good kinetic and fatigue properties as compared with art recognized photochromic compounds of comparative examples CE1 to CE4 having a similar yellow color in the activated (second) state The present invention can be further characterized by one or more of the following non-limiting clauses.

Clause 1. An article which transitions from a first state to a second state in response to electromagnetic radiation, the article comprising an indolenaphthopyran, wherein in the first state the article exhibits a percent transmission of greater than 80 percent, and a b* value of −5 to 15, such as −5 to 10, such as −5 to 5; and in the second state the article exhibits a percent transmission of between 35 and 75 percent, and a $\tau_{SB}$ value of less than 20 percent.

Clause 2. The article of clause 1, wherein in the first state the article exhibits a percent transmission of greater than 80 percent, and a b* value of 0 to 15, such as 0 to 10, such as 0 to 5.

Clause 3. The article of clauses 1 or 2, wherein in the second state, the article exhibits a percent transmission of between 35 and 75 percent, and a $\tau_{SB}$ value of 3.0 percent to less than 20 percent, such as 4.0 percent to less than 20 percent, such as 5.0 percent to less than 20 percent.

Clause 4. The article of clauses 1 through 3, wherein the indolenaphthopyran is a photochromic indolenaphthopyran comprising the core skeletal structure represented by the following Formula (I):

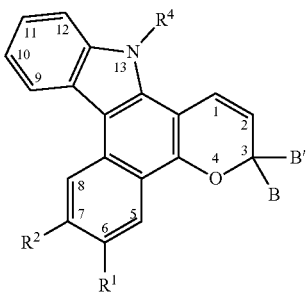

Formula (I)

wherein,
R¹ and R² are each independently hydrogen, substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, a nitrogen containing heterocycle, substituted or unsubstituted alkyl, substituted or unsubstituted aryl, —NHC(O)R$^a$, or —OC(O)R$^a$,
wherein R$^a$ is substituted or unsubstituted alkyl, substituted or unsubstituted aryl, substituted or unsubstituted heteroaryl, substituted or unsubstituted alkoxy, substituted or unsubstituted aryloxy, substituted or unsubstituted alkylthio, or substituted or unsubstituted arylthio;
R⁴ is selected from hydrogen, substituted or unsubstituted alkyl, substituted or unsubstituted heterocycloalkyl, allyl, substituted or unsubstituted aryl, or substituted or unsubstituted heteroaryl; and
B and B' are each independently substituted or unsubstituted aryl, or substituted or unsubstituted heteroaryl, wherein each substituted aryl or substituted heteroaryl is substituted with a group having a Hammett σ$_p$ value of greater than −0.50.

What is claimed is:

1. An article which transitions from a first state to a second state in response to actinic radiation, the article comprising an indolenaphthopyran, wherein
in the first state the article exhibits a percent transmission of greater than 80 percent, and
in the second state the article exhibits a percent transmission of between 35 and 75 percent, and a τ$_{SB}$ value of less than 20 percent.

2. The article of claim 1, which has a b* value in the first state ranging from −5 to 15.

3. The article of claim 1, wherein the indolenaphthopyran is a photochromic indolenaphthopyran comprising the core skeletal structure represented by the following Formula (I):

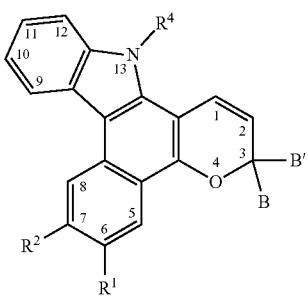

Formula (I)

wherein,
R¹ and R² are each independently hydrogen, substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, a nitrogen containing heterocycle, substituted or unsubstituted alkyl, substituted or unsubstituted aryl, —NHC(O)R$^a$, or —OC(O)R$^a$,
wherein R$^a$ is substituted or unsubstituted alkyl, substituted or unsubstituted aryl, substituted or unsubstituted heteroaryl, substituted or unsubstituted alkoxy, substituted or unsubstituted aryloxy, substituted or unsubstituted alkylthio, or substituted or unsubstituted arylthio;
R⁴ is selected from hydrogen, substituted or unsubstituted alkyl, substituted or unsubstituted heterocycloalkyl, allyl, substituted or unsubstituted aryl, or substituted or unsubstituted heteroaryl; and
B and B' are each independently substituted or unsubstituted aryl, or substituted or unsubstituted heteroaryl, wherein each substituted aryl or substituted heteroaryl is substituted with a group having a Hammett σ$_p$ value of greater than −0.50.

4. The article of claim 3, wherein
R¹ is substituted or unsubstituted alkoxy, and
R² is substituted or unsubstituted alkyloxy, substituted or unsubstituted aryloxy, substituted or unsubstituted alkylthio, substituted or unsubstituted arylthio, substituted or unsubstituted ether, substituted or unsubstituted thioether, amino, or a nitrogen-containing heterocycle.

5. The article of claim 3, wherein B and B' are each independently substituted aryl or substituted heteroaryl with a group having a Hammett σ$_p$ value of −0.5 to 0.8.

6. The article of claim 3, wherein B and B' are each independently substituted or unsubstituted phenyl.

7. The article of claim 6, wherein each phenyl substituent is in each case independently alkoxy, halo, alkyl, or aryloxy.

8. The article of claim 3, wherein R⁴ is substituted or unsubstituted phenyl or substituted or unsubstituted alkyl.

9. The article of claim 1, wherein the indolenaphthopyran has the core skeletal structure represented by Formula (Ia):

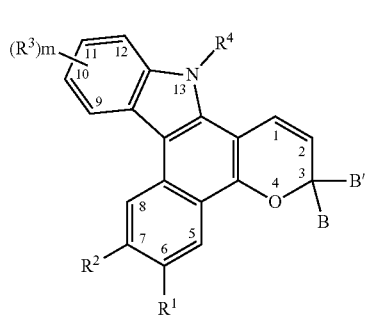

Formula (Ia)

wherein,
m is 0 to 4; and
R³ independently for each m is
i. hydroxyl;
ii. cyano;
iii. (meth)acrylate;
iv. amino or nitrogen-containing heterocycle;
V. a mesogen-containing group L¹;
vi. substituted or unsubstituted alkyl;

vii. substituted or unsubstituted alkenyl;
viii. substituted or unsubstituted alkynyl;
ix. a halo group;
x. a perhalo group;
xi. boronic ester or boronic acid;
xii. polyether, polyester, polycarbonate, or polyurethane;
xiii. substituted or unsubstituted aryl;
xiv. substituted or unsubstituted heterocycloalkyl;
xv. substituted or unsubstituted heteroaryl;
xvi. substituted or unsubstituted alkoxy or substituted or unsubstituted aryloxy;
xvii. substituted or unsubstituted alkylthio or substituted or unsubstituted arylthio;
xviii. ketone, aldehyde, ester, carboxylic acid, carboxylate, or amide;
xix. carbonate, carbamate, or urea; or
xx. siloxane, alkoxysilane, or polysiloxane.

10. The article of claim 9, wherein $R^3$ is at the 11-position.

11. The article of claim 9, wherein $R^3$ is at the 10-position and is a mesogen-containing group $L^1$.

12. The article of claim 9, wherein $R^3$ is cyano; a halo group; haloalkyl; perhaloalkyl; substituted or unsubstituted aryl; or substituted or unsubstituted heteroaryl.

13. The article of claim 9, wherein $R^3$ for each m independently is a mesogen-containing group $L^1$ represented by the following Formula (II),

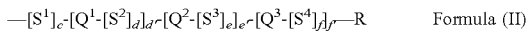  Formula (II)

wherein,
(a) $Q^1$, $Q^2$, and $Q^3$ for each occurrence, are independently a divalent group selected from the group consisting of unsubstituted aryl, substituted aryl, unsubstituted cycloalkyl, and substituted cycloalkyl;
wherein the aryl substituents and cycloalkyl substituents are each independently selected from the group consisting of liquid crystal mesogens, halogen, alkyl, alkoxy, alkylamino, dialkylamino, alkylthio, alkoxycarbonyl, alkylcarbonyl, alkoxycarbonyloxy, aryloxycarbonyloxy, perfluoroalkyl, and perfluoroalkoxy;
(b) c, d, e, and f are each independently an integer of 0 to 3; and each $S^1$, $S^2$, $S^3$, and $S^4$ is independently chosen for each occurrence from a spacer unit selected from the group consisting of:
(i) —C(Z)$_2$—, —N(Z)—, —C(Z)=C(Z)—, —C(Z)=N—, wherein Z for each occurrence is independently selected from the group consisting of hydrogen, alkyl, or aryl;
(ii) —Si(CH$_3$)$_2$—, —Si(CH$_3$)$_2$O—; and
(iii) —O—, —C(=O)—, —C≡C—, —N=N—, —S—, —S(=O)—, —(O=)S(=O)—, —(O=)S(=O)O—, —O(O=)S(=O)O— provided that when two spacer units comprising heteroatoms are linked together the spacer units are linked so that heteroatoms are not directly linked to each other;
(c) R is alkyl; and
(d) d', e' and f' are each independently 0, 1, 2, 3, and 4, provided that the sum of d'+e'+f' is at least 1.

14. The article of claim 1, wherein the indolenaphthopyran has a bimodal absorption profile wherein the A band to B band absorption ratio ranges from 3.0 to 7.0:1.

15. The article of claim 1, wherein the article is a photochromic article selected from the group consisting of ophthalmic articles, display articles, windows, mirrors, active liquid crystal cell articles, and passive liquid crystal cell articles; or
wherein the article is a photochromic ophthalmic article selected from the group consisting of corrective lenses, non-corrective lenses, contact lenses, intra-ocular lenses, magnifying lenses, protective lenses, and visors; or
wherein the article is a photochromic display article selected from the group consisting of screens, monitors, and security elements.

* * * * *

UNITED STATES PATENT AND TRADEMARK OFFICE
CERTIFICATE OF CORRECTION

PATENT NO. : 12,247,035 B2
APPLICATION NO. : 17/416034
DATED : March 11, 2025
INVENTOR(S) : Ryan Stayshich et al.

Page 1 of 1

It is certified that error appears in the above-identified patent and that said Letters Patent is hereby corrected as shown below:

In the Claims

Column 60, Line 66, Claim 9, delete "V." and insert -- v. --

Column 62, Line 13, Claim 13, delete "-(O=) S(=O)O) -," and insert -- -(O=)S(=O)O-, --

Signed and Sealed this
Sixth Day of May, 2025

Coke Morgan Stewart
*Acting Director of the United States Patent and Trademark Office*